(12) United States Patent
Wood et al.

(10) Patent No.: US 12,365,937 B2
(45) Date of Patent: Jul. 22, 2025

(54) ASYMMETRIC TARGETED AMPLIFICATION METHODS

(71) Applicant: INTEGRATED DNA TECHNOLOGIES, INC., Coralville, IA (US)

(72) Inventors: Ashley M. Wood, Ann Arbor, MI (US); Jordan Rosefigura, Ann Arbor, MI (US); Vladimir Makarov, Ann Arbor, MI (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 1125 days.

(21) Appl. No.: 17/182,937

(22) Filed: Feb. 23, 2021

(65) Prior Publication Data

US 2021/0180121 A1    Jun. 17, 2021

Related U.S. Application Data

(63) Continuation of application No. PCT/US2019/047905, filed on Aug. 23, 2019.

(60) Provisional application No. 62/722,366, filed on Aug. 24, 2018.

(51) Int. Cl.
| | | |
|---|---|---|
| *C12Q 1/6848* | (2018.01) | |
| *C12Q 1/6806* | (2018.01) | |
| *C12Q 1/686*  | (2018.01) | |
| *C12Q 1/6869* | (2018.01) | |

(52) U.S. Cl.
CPC ......... *C12Q 1/6848* (2013.01); *C12Q 1/6806* (2013.01); *C12Q 1/686* (2013.01); *C12Q 1/6869* (2013.01)

(58) Field of Classification Search
None
See application file for complete search history.

(56) References Cited

U.S. PATENT DOCUMENTS

| | | |
|---|---|---|
| 2016/0024493 A1 | 1/2016 | Robins |
| 2018/0002738 A1 | 1/2018 | Wang et al. |
| 2018/0087051 A1 | 3/2018 | Apte et al. |

FOREIGN PATENT DOCUMENTS

| | | | | |
|---|---|---|---|---|
| WO | WO-2016118719 A1 | * | 7/2016 | ............ C12Q 1/686 |
| WO | 2018013598 A1 | | 1/2018 | |
| WO | 2018018008 A1 | | 1/2018 | |

OTHER PUBLICATIONS

Schenk et al. "Amplification of overlapping DNA amplicons in a single-tube multiplex PCR for targeted next-generation sequencing of BRCA1 and BRCA2," PLoS One, Jul. 12, 2017, p. 1-16, vol. 12, No. 7.

(Continued)

*Primary Examiner* — Kaijiang Zhang
(74) *Attorney, Agent, or Firm* — BARNES & THORNBURG LLP

(57) ABSTRACT

The present disclosure provides kits and methods for a targeted NGS library workflow comprising a multiplexed PCR for target amplification followed by an indexing PCR for incorporation of NGS adapter sequences. This workflow enables overlapping primer pairs in a single tube for contiguous coverage over target regions, while simultaneously preventing amplification of both primer dimers and undesirable mini-amplicons that result from overlapping primer pairs.

20 Claims, 14 Drawing Sheets

Specification includes a Sequence Listing.

(56) References Cited

OTHER PUBLICATIONS

International Search Report dated Nov. 29, 2021, prepared in International Application No. PCT/US2019/047905.
International Preliminary Report on Patentability dated Mar. 2, 2021, prepared in International Application No. PCT/US2019/047905.

* cited by examiner

Fig. 9

PCR I: multiplex PCR using target specific primers and universal primer

P7tr       P5tr     Forward     Reverse     P7tr

5'-TCAGACGTGTGCTCTTCCGATCT-CGACGCTCTTCCGATCT ———————→ ←——————— TCTAGCCTTCTCGTGTGCAGACT-5'

5'-TCAGACGTGTGCTCTTCCGATCT-CGACGCTCTTCCGATCT ——————— AGATCGGAAGAGCACACGTCTGA-3'
3'AGTCTGCACACGAGAAGGCTAGA-GCTCGAGAAGGCTAGA ——————— TCTAGCCTTCTCGTGTGCAGACT-5'
         P7tr

5'-TCAGACGTGTGCTCTTCCGATCT-3'

5'-TCAGACGTGTGCTCTTCCGATCT-CGACGCTCTTCCGATCT ——————— AGATCGGAAGAGCACACGTCTGA-3'
3'AGTCTGCACACGAGAAGGCTAGA-GCTCGAGAAGGCTAGA ——————— TCTAGCCTTCTCGTGTGCAGACT-5'
             3'-TCTAGCCTTCTCGTGTGCAGACT-5'
             P7tr

PCR II: Indexing PCR using P5tr sequence

5'-TCAGACGTGTGCTCTTCCGATCT
3'AGTCTGCACACGAGAAGGCTAGA-GCTCGAGAAGGCTAGA ——————— AGATCGGAAGAGCACACGTCTGA-3'
    P5       CGACGCTCTTCCGATCT ——————— TCTAGCCTTCTCGTGTGCAGACT-5'

5'-TCAGACGTGTGCTCTTCCGATCT-CGACGCTCTTCCGATCT ——————— AGATCGGAAGAGCACACGTCTGA-3'
3'AGTCTGCACACGAGAAGGCTAGA-GCTCGAGAAGGCTAGA ——————— TCTAGCCTTCTCGTGTGCAGACT-5'
    P5

CGACGCTCTTCCGATCT ——————— AGATCGGAAGAGCACACGTCTGA-3'
3'AGTCTGCACACGAGAAGGCTAGA-GCTCGAGAAGGCTAGA ——————— TCTAGCCTTCTCGTGTGCAGACT
    P5                                                             Indexing primer P7

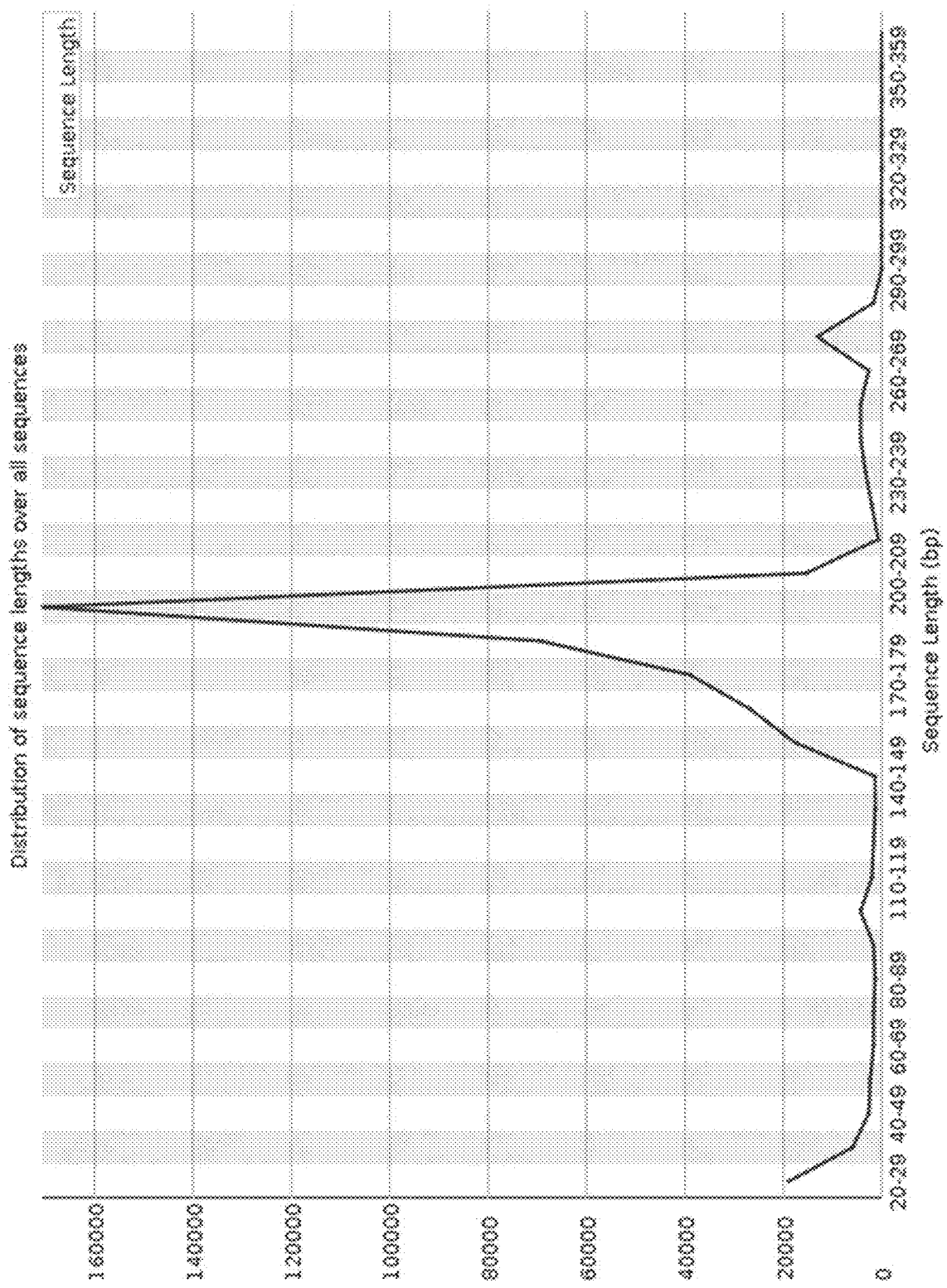

SEQUENCE LISTING

<160> NUMBER OF SEQ ID NOS: 231

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tcagacgtgt gctcttccga tct                                    23

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caagcagaag acggcatacg agatagcttc aggtgactgg agttcagacg tgtgctcttc    60
cgatct                                                              66

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aatgatacgg cgaccaccga gatctacaca tagaggcaca ctctttccct acacgacgct    60
cttccgatct                                                          70

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcagacgtgt gctcttccga tctcgacgct cttccgatct tagcactgcc caacaacacc    60

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 5
tcagacgtgt gctcttccga tctnnnnnnn nnnagactta gtacctgaag ggtga         55

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcagacgtgt gctcttccga tctcgacgct cttccgatct tgggacggaa cagctttgag    60

```
<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 7
tcagacgtgt gctcttccga tctnnnnnnn nnnccaccgc ttcttgtcct g            51

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcagacgtgt gctcttccga tctcgacgct cttccgatct gggtgcagtt atgcctcag    59

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 9
tcagacgtgt gctcttccga tctnnnnnnn nnncggcatt ttgagtgtta gactgg       56

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcagacgtgt gctcttccga tctcgacgct cttccgatct ctgactgctc ttttcaccca   60
t                                                                  61

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 11
tcagacgtgt gctcttccga tctnnnnnnn nnngagcagc ctctggcatt ctg          53
```

```
<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcagacgtgt gctcttccga tctcgacgct cttccgatct tgaagaccca ggtccagatg    60
a                                                                    61

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 13
tcagacgtgt gctcttccga tctnnnnnnn nnngctgccc tggtaggttt tctg           54

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcagacgtgt gctcttccga tctcgacgct cttccgatct gcatcttatc cgagtggaag    60
g                                                                    61

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 15
tcagacgtgt gctcttccga tctnnnnnnn nnncactgac aaccaccctt aacc           54

<210> SEQ ID NO 16
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcagacgtgt gctcttccga tctcgacgct cttccgatct catgtgtaac agttcctgca    60
tg                                                                   62
```

```
<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 17
tcagacgtgt gctcttccga tctnnnnnnn nnnggtcaga ggcaagcaga g            51

<210> SEQ ID NO 18
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcagacgtgt gctcttccga tctcgacgct cttccgatct caggtaggac ctgatttcct   60
tac                                                                 63

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 19
tcagacgtgt gctcttccga tctnnnnnnn nnnttcttgc ggagattctc ttcc         54

<210> SEQ ID NO 20
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcagacgtgt gctcttccga tctcgacgct cttccgatct atggttctat gactttgcct   60
ga                                                                  62

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 21
tcagacgtgt gctcttccga tctnnnnnnn nnnagcaggc taggctaagc tatg         54
```

<210> SEQ ID NO 22
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcagacgtgt gctcttccga tctcgacgct cttccgatct ctgtgcagct gtgggttga        59

<210> SEQ ID NO 23
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 23
tcagacgtgt gctcttccga tctnnnnnnn nnngctcacc atcgctatct gag        53

<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcagacgtgt gctcttccga tctcgacgct cttccgatct agctggggct ggagaga        57

<210> SEQ ID NO 25
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 25
tcagacgtgt gctcttccga tctnnnnnnn nnngtcatcc aaatactcca cacgca        56

<210> SEQ ID NO 26
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcagacgtgt gctcttccga tctcgacgct cttccgatct ctctgtctcc ttcctcttcc        60
tac        63

<210> SEQ ID NO 27
<211> LENGTH: 53

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 27
tcagacgtgt gctcttccga tctnnnnnnn nnngtgctgt gactgcttgt aga            53

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcagacgtgt gctcttccga tctcgacgct cttccgatct cgcactggcc tcatcttg      58

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 29
tcagacgtgt gctcttccga tctnnnnnnn nnncttccag tgtgatgatg gtgag          55

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcagacgtgt gctcttccga tctcgacgct cttccgatct catgacggag gttgtgagg     59

<210> SEQ ID NO 31
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 31
tcagacgtgt gctcttccga tctnnnnnnn nnnagcaatc agtgaggaat cagag          55

<210> SEQ ID NO 32
<211> LENGTH: 63
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 32
tcagacgtgt gctcttccga tctcgacgct cttccgatct cctggttgta gctaactaac    60
ttc                                                                  63

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 33
tcagacgtgt gctcttccga tctnnnnnnn nnnaccatcg taagtcaagt agcatc        56

<210> SEQ ID NO 34
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcagacgtgt gctcttccga tctcgacgct cttccgatct cctccctgc ttctgtctc      59

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 35
tcagacgtgt gctcttccga tctnnnnnnn nnnctgtcag tggggaacaa gaag          54

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcagacgtgt gctcttccga tctcgacgct cttccgatct gctgaatgag gccttggaac    60

<210> SEQ ID NO 37
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<220> FEATURE:
<221> NAME/KEY: modified_base
<222> LOCATION: (24)..(33)
<223> OTHER INFORMATION: a, c, t, g, unknown or other

<400> SEQUENCE: 37
tcagacgtgt gctcttccga tctnnnnnnn nnnctttcca acctaggaag gcag    54

<210> SEQ ID NO 38
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcagacgtgt gctcttccga tctcgacgct cttccgatct tcttgcagca gccagact    58

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 39
tcagacgtgt gctcttccga tctnnnnnnn nnncctgccc ttccaatgga tc    52

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcagacgtgt gctcttccga tctcgacgct cttccgatct ttacttctcc ccctcctctg    60

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 41
tcagacgtgt gctcttccga tctnnnnnnn nnncttccca gcctgggcat c    51

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcagacgtgt gctcttccga tctcgacgct cttccgatct ctggcccctg tcatcttctg    60

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 43
tcagacgtgt gctcttccga tctnnnnnnn nnncaggcat tgaagtctca tgga    54

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 44
tcagacgtgt gctcttccga tctcgacgct cttccgatct ccccctagcag agacctgt    58

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (24)..(33)
<223> OTHER INFORMATION: a, c, t, g, unknown or other

<400> SEQUENCE: 45
tcagacgtgt gctcttccga tctnnnnnnn nnngcccaac ccttgtcctt ac    52

<210> SEQ ID NO 46
<211> LENGTH: 74
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 46
caagcagaag acggcatacg agataatgag cggtgactgg agttcagacg tgtgctcttc    60
cgatctgcgc gcgg    74

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 47
aatgatacgg cgaccaccga gatctacacc ctatcctaca ctctttccct acacgacgct    60
cttccgatct    70

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccctacacga cgctcttccg atctgcgcgc ggtgatggca aatacacaga ggaag          55

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccctacacga cgctcttccg atctcaggat tcttacagaa aacaagtggt                50

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccctacacga cgctcttccg atctgcgcgc ggcagagtaa cagactagct agagacaatg     60

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccctacacga cgctcttccg atctagcact tacctgtgac tccatag                   47

<210> SEQ ID NO 52
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ccctacacga cgctcttccg atctgcgcgc gggccagaac tacaatcttt tgatgaca       58

<210> SEQ ID NO 53
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ccctacacga cgctcttccg atctattgtg tggaagatcc aatccat                   47

```
<210> SEQ ID NO 54
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccctacacga cgctcttccg atctgcgcgc ggattcacag agacttggca gcc          53

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ccctacacga cgctcttccg atctgtcaag cagagaatgg gtactcac                48

<210> SEQ ID NO 56
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccctacacga cgctcttccg atctgcgcgc ggagcttgtg gagcctctta ca           52

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccctacacga cgctcttccg atctgggacc ttaccttata caccgt                  46

<210> SEQ ID NO 58
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccctacacga cgctcttccg atctgcgcgc gggatcccag aaggtgagaa agtt         54

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccctacacga cgctcttccg atcttgaggt tcagagccat gga                     43

<210> SEQ ID NO 60
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ccctacacga cgctcttccg atctgcgcgc ggctccagga agcctacgtg a            51

<210> SEQ ID NO 61
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccctacacga cgctcttccg atctggacat agtccaggag gca                    43

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccctacacga cgctcttccg atctcaccgc agcatgtcaa gatc                   44

<210> SEQ ID NO 63
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccctacacga cgctcttccg atctgcgcgc gggacctaaa gccacctcct tac         53

<210> SEQ ID NO 64
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccctacacga cgctcttccg atctgcgcgc ggggatccag acaactgttc aaactg      56

<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccctacacga cgctcttccg atctgttttc ctttacttac tacacctca              49

<210> SEQ ID NO 66
<211> LENGTH: 61
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccctacacga cgctcttccg atctgcgcgc gggcatatta aacaagatt tacctctatt      60
g                                                                    61

<210> SEQ ID NO 67
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccctacacga cgctcttccg atctataagg cctgctgaaa atgactg                   47

<210> SEQ ID NO 68
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccctacacga cgctcttccg atctgcgcgc ggctagctct tcaccctgca aaaata         56

<210> SEQ ID NO 69
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ccctacacga cgctcttccg atctgcgcgc ggaaaatcgt tgtgtttca catgaaa         57

<210> SEQ ID NO 70
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ccctacacga cgctcttccg atctgcgcgc ggaggaaaac aacgagaata aatcaaa        57

<210> SEQ ID NO 71
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ccctacacga cgctcttccg atctgcgcgc ggactctcta gataatgatg aatgtagca      59

<210> SEQ ID NO 72
```

<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
ccctacacga cgctcttccg atctgcgcgc ggtgtctgga ttggagaaag tttctaa    57

<210> SEQ ID NO 73
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
ccctacacga cgctcttccg atctgcgcgc gggtataggg aagcttcata agtcagt    57

<210> SEQ ID NO 74
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
ccctacacga cgctcttccg atctgcgcgc ggattacaaa acgcaagaca agtgtt    56

<210> SEQ ID NO 75
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
ccctacacga cgctcttccg atctgcgcgc ggattcagac cagctcacaa gagaag    56

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
ccctacacga cgctcttccg atctgcgcgc ggaaggcttt tcatataatg tggtaaa    57

<210> SEQ ID NO 77
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
ccctacacga cgctcttccg atctgcgcgc gggagtgtta gaggaatttg atttaa    56

<210> SEQ ID NO 78
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccctacacga cgctcttccg atctctgtct gtaaatatgt ctttcact                   48

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ccctacacga cgctcttccg atctaacaac ctgccataat tttcgttt                   48

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccctacacga cgctcttccg atctatgtca gcaaaaacct tatgtgaa                   48

<210> SEQ ID NO 81
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ccctacacga cgctcttccg atcttttcca aactaacatc acaaggt                    47

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccctacacga cgctcttccg atcttgtgct aaaaatccca caagtatt                   48

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ccctacacga cgctcttccg atctaagact tgcttggtac tatcttct                   48

<210> SEQ ID NO 84
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 84
ccctacacga cgctcttccg atctttctgg agtacgtata gcagtatt          48

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccctacacga cgctcttccg atctcttgct gtactaaatc cagagaaa          48

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccctacacga cgctcttccg atcttagtga agactatgct cagttctg          48

<210> SEQ ID NO 87
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccctacacga cgctcttccg atctttactg caggtttttt ccatttct          48

<210> SEQ ID NO 88
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccatctcatc cctgcgtgtc tccgactcag ctaaggtaac agcaggatcg gtatggc    57

<210> SEQ ID NO 89
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cctctctatg ggcagtcggt gattcagacg tgtgctcttc cgatct           46

<210> SEQ ID NO 90
<211> LENGTH: 65
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 90
tcagacgtgt gctcttccga tctagcagga tcggtatggc aagtataccc ctgacaggga    60
aacaa                                                                65

<210> SEQ ID NO 91
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tcagacgtgt gctcttccga tctaacattt tcctggatgt acttgctg                 48

<210> SEQ ID NO 92
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tcagacgtgt gctcttccga tctagcagga tcggtatggc tgtgttgtat ttccagcagt    60
tcaaa                                                                65

<210> SEQ ID NO 93
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tcagacgtgt gctcttccga tctcttcaca gcctgctata cctactag                 48

<210> SEQ ID NO 94
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tcagacgtgt gctcttccga tctagcagga tcggtatggc gaggctgatc atgaggaatc    60
tctg                                                                 64

<210> SEQ ID NO 95
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tcagacgtgt gctcttccga tctttcaccc agtcttccat atcattct                 48
```

<210> SEQ ID NO 96
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tcagacgtgt gctcttccga tctagcagga tcggtatggc gcacttctcc tacttaggtc      60
acttt                                                                  65

<210> SEQ ID NO 97
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tcagacgtgt gctcttccga tctgggtttt tacaatgaac aacacagc                   48

<210> SEQ ID NO 98
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tcagacgtgt gctcttccga tctagcagga tcggtatggc gactgttact agcgggcttt      60
tcttg                                                                  65

<210> SEQ ID NO 99
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tcagacgtgt gctcttccga tctcaagcca gcaaccacag aaac                       44

<210> SEQ ID NO 100
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcagacgtgt gctcttccga tctagcagga tcggtatggc gatgatgaca tcctgagccc      60
aag                                                                    63

<210> SEQ ID NO 101
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 101
tcagacgtgt gctcttccga tctcagatct cttctcataa gggcactg          48

<210> SEQ ID NO 102
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tcagacgtgt gctcttccga tctagcagga tcggtatggc cacccatcat ccccactcac    60

<210> SEQ ID NO 103
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tcagacgtgt gctcttccga tcttctgctc cctgggatga gaag              44

<210> SEQ ID NO 104
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tcagacgtgt gctcttccga tctagcagga tcggtatggc tgttgcttgt cattctccag    60
atcta                                                                65

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tcagacgtgt gctcttccga tctcaaaagg aaatggtgcc tttttcag          48

<210> SEQ ID NO 106
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcagacgtgt gctcttccga tctagcagga tcggtatggc tagggcgta tcaaaaccaa    60 gaata                                                                65

<210> SEQ ID NO 107
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 107
tcagacgtgt gctcttccga tcttgactag ctagagtatc aaaagggt                    48

<210> SEQ ID NO 108
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tcagacgtgt gctcttccga tctagcagga tcggtatggc aatccctctc tacttacctg       60
gtttg                                                                   65

<210> SEQ ID NO 109
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tcagacgtgt gctcttccga tcttgtttag caggttcagg gtcac                       45

<210> SEQ ID NO 110
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tcagacgtgt gctcttccga tctagcagga tcggtatggc accttctact gtgttcttat       60
aggca                                                                   65

<210> SEQ ID NO 111
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tcagacgtgt gctcttccga tctcagtcaa ggatctgtac tctccttg                    48

<210> SEQ ID NO 112
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tcagacgtgt gctcttccga tctagcagga tcggtatggc cctcaaccag aaaacatcaa       60
gattt                                                                   65
```

<210> SEQ ID NO 113
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcagacgtgt gctcttccga tcttggcatt ctttatcttc acatcaac            48

<210> SEQ ID NO 114
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tcagacgtgt gctcttccga tctagcagga tcggtatggc aagccaccac tgtgaccac    59

<210> SEQ ID NO 115
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tcagacgtgt gctcttccga tctgacctcc acctctagga cctg                44

<210> SEQ ID NO 116
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tcagacgtgt gctcttccga tctagcagga tcggtatggc aacagaacga aaagaaagt    60 ggctc                                                               65

<210> SEQ ID NO 117
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcagacgtgt gctcttccga tctctcaaac tgtgataagc tgcacttg            48

<210> SEQ ID NO 118
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tcagacgtgt gctcttccga tctagcagga tcggtatggc ttcccaaaga tgcagaacta    60
caaag                                                              65

<210> SEQ ID NO 119
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcagacgtgt gctcttccga tctgtgactc agacttgtcc cagg                    44

<210> SEQ ID NO 120
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tcagacgtgt gctcttccga tctagcagga tcggtatggc agacagtagt aataacagca   60
agggc                                                              65

<210> SEQ ID NO 121
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tcagacgtgt gctcttccga tctcattatg gggatcttct ttgccttc                48

<210> SEQ ID NO 122
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tcagacgtgt gctcttccga tctagcagga tcggtatggc ccataagaaa tgcctgggaa   60
acc                                                                63

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tcagacgtgt gctcttccga tctgtagaga atgtggcttc atcctc                  46

<210> SEQ ID NO 124
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
tcagacgtgt gctcttccga tctagcagga tcggtatggc gggtacaagt atgtgaaaca    60
aaggg    65

<210> SEQ ID NO 125
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tcagacgtgt gctcttccga tctctctgga cttgttggag aaggcatt    48

<210> SEQ ID NO 126
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tcagacgtgt gctcttccga tctagcagga tcggtatggc tgttctctgg tagttcctct    60
tcag    64

<210> SEQ ID NO 127
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tcagacgtgt gctcttccga tctttgtttc ttaaaggctg ctcttgag    48

<210> SEQ ID NO 128
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tcagacgtgt gctcttccga tctagcagga tcggtatggc tcacacatag cacacgtggt    60

<210> SEQ ID NO 129
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tcagacgtgt gctcttccga tctatgccga tgggattgac atgg    44

<210> SEQ ID NO 130
<211> LENGTH: 65
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 130
tcagacgtgt gctcttccga tctagcagga tcggtatggc ttttgcataa cttggggtgt    60
aagag                                                                65

<210> SEQ ID NO 131
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tcagacgtgt gctcttccga tctctagatc cccaaacttc tgccttc                  47

<210> SEQ ID NO 132
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tcagacgtgt gctcttccga tctagcagga tcggtatggc gggagcatat tatggcagtg    60
ga                                                                   62

<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcagacgtgt gctcttccga tctcactgag ttctaaaatg ccagaagg                 48

<210> SEQ ID NO 134
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tcagacgtgt gctcttccga tctagcagga tcggtatggc ctcaggagaa gagactcaca    60
cag                                                                  63

<210> SEQ ID NO 135
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tcagacgtgt gctcttccga tcttacctaa gcacatttaa aggggggaa                48
```

<210> SEQ ID NO 136
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tcagacgtgt gctcttccga tctagcagga tcggtatggc ctaagatcag ctccctttgt    60
ctgt    64

<210> SEQ ID NO 137
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tcagacgtgt gctcttccga tctttggcaa tgtagacact ggtcag    46

<210> SEQ ID NO 138
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tcagacgtgt gctcttccga tctagcagga tcggtatggc gtactcgtgt ctcacagtgt    60
gtc    63

<210> SEQ ID NO 139
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tcagacgtgt gctcttccga tctattattt cccacccttc ccactttc    48

<210> SEQ ID NO 140
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tcagacgtgt gctcttccga tctagcagga tcggtatggc agggttatag gcacaaattc    60
tcctt    65

<210> SEQ ID NO 141
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tcagacgtgt gctcttccga tcttgtcttc gttttaattg ccaagcag                48

<210> SEQ ID NO 142
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tcagacgtgt gctcttccga tctagcagga tcggtatggc ccaaactgca tgactctctt    60
tgtac                                                                65

<210> SEQ ID NO 143
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tcagacgtgt gctcttccga tctggcggca acaacagatt gaac                    44

<210> SEQ ID NO 144
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tcagacgtgt gctcttccga tctagcagga tcggtatggc taggaagagt taatcacgtg    60
cttca                                                                65

<210> SEQ ID NO 145
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tcagacgtgt gctcttccga tctatgaagg ccttattttc atctgcag                48

<210> SEQ ID NO 146
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tcagacgtgt gctcttccga tctagcagga tcggtatggc cacaggacta tgacatcacc    60
cag                                                                  63

<210> SEQ ID NO 147

-continued

```
<210> SEQ ID NO 147
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcagacgtgt gctcttccga tctcctcacc tcaattataa agttgccg              48

<210> SEQ ID NO 148
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tcagacgtgt gctcttccga tctagcagga tcggtatggc ggaggaaaag atactcatcc  60
cttct                                                              65

<210> SEQ ID NO 149
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tcagacgtgt gctcttccga tctttcttgg ctatggatgg agtaagc                47

<210> SEQ ID NO 150
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tcagacgtgt gctcttccga tctagcagga tcggtatggc tttagttctg tgccttcccc  60
tg                                                                 62

<210> SEQ ID NO 151
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tcagacgtgt gctcttccga tctgagcagg tagagctgtg tgg                    43

<210> SEQ ID NO 152
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tcagacgtgt gctcttccga tctagcagga tcggtatggc tggattcttc tagttcccga  60
``` tacag                                                             65

<210> SEQ ID NO 153
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tcagacgtgt gctcttccga tctcataaac ccgtaatgtg aagcctg               47

<210> SEQ ID NO 154
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tcagacgtgt gctcttccga tctagcagga tcggtatggc actttcttaa tccctcctca  60
tgcaa                                                             65

<210> SEQ ID NO 155
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tcagacgtgt gctcttccga tctcaacctg aaattgctgc aggaag                46

<210> SEQ ID NO 156
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tcagacgtgt gctcttccga tctagcagga tcggtatggc gatgctggca ggggaggctg  60
taaag                                                             65

<210> SEQ ID NO 157
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tcagacgtgt gctcttccga tctcacaagg actgcaagtt cctgatc               47

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
tcagacgtgt gctcttccga tctagcagga tcggtatggc ctcccctttt agcccaggta    60

<210> SEQ ID NO 159
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tcagacgtgt gctcttccga tctgtggttc cttttcaggc actataac    48

<210> SEQ ID NO 160
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tcagacgtgt gctcttccga tctagcagga tcggtatggc agtccttgcc cttcttaata    60
agca    64

<210> SEQ ID NO 161
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tcagacgtgt gctcttccga tctcataaca acttcttcaa gctgcaga    48

<210> SEQ ID NO 162
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tcagacgtgt gctcttccga tctagcagga tcggtatggc tgagcggaaa ttaatcttca    60
agtttt    66

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tcagacgtgt gctcttccga tctgtcattc cagatttgtt gtgtgtac    48

<210> SEQ ID NO 164
<211> LENGTH: 68
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 164
tcagacgtgt gctcttccga tctagcagga tcggtatggc aggaaaacaa tttaagtaag    60
gaaactcc                                                             68

<210> SEQ ID NO 165
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tcagacgtgt gctcttccga tcttttccca ttacactcct tcagatgt                 48

<210> SEQ ID NO 166
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tcagacgtgt gctcttccga tctagcagga tcggtatggc gagaactgag cgaagggaaa    60
aga                                                                  63

<210> SEQ ID NO 167
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tcagacgtgt gctcttccga tctctggtcc acagtgtacc taacttc                  47

<210> SEQ ID NO 168
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tcagacgtgt gctcttccga tctagcagga tcggtatggc taaagacatg aagtacccca    60
ttgct                                                                65

<210> SEQ ID NO 169
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tcagacgtgt gctcttccga tctgatgtag taatgcatgc catacagc                 48

<210> SEQ ID NO 170
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 170
tcagacgtgt gctcttccga tctagcagga tcggtatggc cttcatgtgt taacctgggg    60
atgat    65

<210> SEQ ID NO 171
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 171
tcagacgtgt gctcttccga tctttaacaa ctcttgtcca agaaggc    48

<210> SEQ ID NO 172
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 172
tcagacgtgt gctcttccga tctagcagga tcggtatggc atttggaact gactgtactt    60
tctgc    65

<210> SEQ ID NO 173
<211> LENGTH: 47
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 173
tcagacgtgt gctcttccga tcttactcac ctctgccact tgatctt    47

<210> SEQ ID NO 174
<211> LENGTH: 64
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 174
tcagacgtgt gctcttccga tctagcagga tcggtatggc ctccccctct tcatcatctt    60
cttc    64

<210> SEQ ID NO 175
<211> LENGTH: 48
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 175
tcagacgtgt gctcttccga tcttagctag catacttcct cacatgtg        48

<210> SEQ ID NO 176
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tcagacgtgt gctcttccga tctagcagga tcggtatggc tgtctttcca tgtgtcttta        60
tgctg        65

<210> SEQ ID NO 177
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tcagacgtgt gctcttccga tctcattctc tccagtggaa gagacac        47

<210> SEQ ID NO 178
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tcagacgtgt gctcttccga tctagcagga tcggtatggc gaggcctctg actgtatcac        60
tattt        65

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tcagacgtgt gctcttccga tctaagccaa ggggtctctt ca        42

<210> SEQ ID NO 180
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tcagacgtgt gctcttccga tctagcagga tcggtatggc aggtcaaatg gcaaaggtaa        60
aacc        64

<210> SEQ ID NO 181

```
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tcagacgtgt gctcttccga tctctgagga tggcagctga gatt            44

<210> SEQ ID NO 182
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tcagacgtgt gctcttccga tctagcagga tcggtatggc aaacatgatg gacaacagaa    60
ctact                                                                65

<210> SEQ ID NO 183
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tcagacgtgt gctcttccga tctctgattg gagggctgg taaag             45

<210> SEQ ID NO 184
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcagacgtgt gctcttccga tctagcagga tcggtatggc ggaagattta gaacagctga    60
agcag                                                                65

<210> SEQ ID NO 185
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tcagacgtgt gctcttccga tctatcttcc ctcgcccct g                 41

<210> SEQ ID NO 186
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tcagacgtgt gctcttccga tctagcagga tcggtatggc ggactcatgt atgtctactg    60
``` gactc                                                              65

<210> SEQ ID NO 187
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tcagacgtgt gctcttccga tctcttacct cttgactgcc tgctg              45

<210> SEQ ID NO 188
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tcagacgtgt gctcttccga tctagcagga tcggtatggc cagttcattg agtactgtaa    60
gctgg                                                              65

<210> SEQ ID NO 189
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tcagacgtgt gctcttccga tctgtgaagg caaaaaggat gtccaag            47

<210> SEQ ID NO 190
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cctacacgac gctcttccga tctgcgcgcg g                              31

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cctacacgac gctcttccga tct                                       23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agatcggaag agcgtcgtgt agg					23

<210> SEQ ID NO 193
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ccgcgcgcag atcggaagag cgtcgtgtag g					31

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gctcttccga tctgcgcgcg g					21

<210> SEQ ID NO 195
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cctacacgac gctcttccga tctcgcgtgc tcttccgatc t					41

<210> SEQ ID NO 196
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
agatcggaag agcacgcgag atcggaagag cgtcgtgtag g					41

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cgcgtgctct tccgatct					18

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tcagacgtgt gctcttccga tctcgacgct cttccgatct                           40

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tcagacgtgt gctcttccga tct                                            23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agatcggaag agcacacgtc tga                                            23

<210> SEQ ID NO 201
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
tcagacgtgt gctcttccga tctggg                                         26

<210> SEQ ID NO 202
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tcagacgtgt gctcttccga tctacgacgc tcttccgatc tggg                     44

<210> SEQ ID NO 203
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tcagacgtgt gctcttccga tctggggggg ggggggggg g                         41

<210> SEQ ID NO 204
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tcagacgtgt gctcttccga tctcgacgct cttccgatct ggg                43

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tcagacgtgt gctcttccga tctgacgctc ttccgatctg gg                 42

<210> SEQ ID NO 206
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
cctacacgac gctcttccga tctgggggggg gggggggggg g                 41

<210> SEQ ID NO 207
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cctacacgac gctcttccga tctacgtgtg ctcttccgat ctggg              45

<210> SEQ ID NO 208
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cctacacgac gctcttccga tctcgtgtgc tcttccgatc tggg               44

<210> SEQ ID NO 209
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
cctacacgac gctcttccga tctgtgtgct cttccgatct ggg                43

<210> SEQ ID NO 210
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
cctacacgac gctcttccga tctgcgcgcg gggg                          34

<210> SEQ ID NO 211
<211> LENGTH: 43
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 211
cctacacgac gctcttccga tctgctcttc cgatctgcgc ggg          43

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 212
cctacacgac gctcttccga tctgctcttc cgatctgcgg gg           42

<210> SEQ ID NO 213
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 213
cctacacgac gctcttccga tctgctcttc cgatctgcgg g            41

<210> SEQ ID NO 214
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 214
aatgatacgg cgaccaccga gatctacac                          29

<210> SEQ ID NO 215
<211> LENGTH: 33
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 215
acactctttc cctacacgac gctcttccga tct                     33

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 216
caagcagaag acggcatacg agat                               24

<210> SEQ ID NO 217
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gtgactggag ttcagacgtg tgctcttccg atct                              34

<210> SEQ ID NO 218
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gtgactggag ttcagacgtg tgctcttccg atctgcgcgc gg                     42

<210> SEQ ID NO 219
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
gtgactggag ttcagacgtg tgctcttccg atctgcgc                          38

<210> SEQ ID NO 220
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
gtgactggag ttcagacgtg tgctcttccg atctgcg                           37

<210> SEQ ID NO 221
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gtgactggag ttcagacgtg tgctcttccg atctgc                            36

<210> SEQ ID NO 222
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
cctctctatg ggcagtcggt gatggg                                       26

```
<210> SEQ ID NO 223
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cctctctatg ggcagtcggt gatcgatgcg cgcggggg                              38

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
cctctctatg ggcagtcggt gat                                              23

<210> SEQ ID NO 225
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ccactacgcc tccgctttcc tctctatggg cagtcggtga t                          41

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccatctcatc cctgcgtgtc tccgactcag                                       30

<210> SEQ ID NO 227
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cgatgcgcgc gg                                                          12

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tcagacgtgt gctcttccga tct                                              23

<210> SEQ ID NO 229
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
agatcggaag agcacacgtc tga                                              23

<210> SEQ ID NO 230
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
agatcggaag agctcgagat cggaagagca cacgtctga                             39

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cgacgctctt ccgatct                                                     17
```

ASYMMETRIC TARGETED AMPLIFICATION METHODS

CROSS-REFERENCE TO RELATED APPLICATIONS

The present application is a continuation of International Application No. PCT/US2019/047905, filed Aug. 23, 2019, published as WO 2020/041702, which claims priority to U.S. Provisional Application No. 62/722,366, filed Aug. 24, 2018, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created Aug. 20, 2019, is named 18-21013-WO_SL.txt and 60,954 bytes in size.

BACKGROUND

Amplicon sequencing is one of the leading technologies for targeted next generation sequencing. One trend in this technology is to use a multiplex polymerase chain reaction (PCR) approach to amplify multiple target regions in a single tube. Amplicon sequencing is the method of choice for rapid turnaround time given the reduced number of steps, for when panels of target loci significantly smaller than whole exomes are desired, and for significant overall cost savings in both preparative reagents and sequencing cost. Amplicon sequencing is represented by a variety of available techniques. A basic workflow is depicted in FIG. 1 where target specific primers are used for target enrichment, followed by an adapter ligation step to complete the NGS library. FIG. 2 depicts an alternative method where partial NGS adapter sequences A and B are incorporated as 5' tails on each forward and reverse target specific primer during a first PCR, followed by completion of the NGS adapter using indexing PCR with primers that anneal to the partial adapter sequence introduced in the first PCR. However, both of these methods result in significant primer dimer formation, a common artifact of multiplex PCR, which is undesirable because it increases the cost of sequencing when significant primer dimer content is present in the final NGS library. Additionally, undesired short amplicon artifacts can also dominate the resulting NGS amplicon library and sequencing data.

The prior art means to address the primer dimer/undesired amplicon artifact problems generally result in a decrease in efficiency and/or accuracy. Specifically, these prior art methods (1) require qPCR quantification, (2) require synthetic sequences in the target primers and (3) require low base composition complexity sequences at the junction of the NGS adaptors.

Thus, what is needed is a high multiplexing capacity, such as combining thousands of primer pairs into a single reaction, that avoids the above-mentioned sequencing artifacts and decreased efficiency and/or accuracy. The compositions and methods disclosed herein provide a novel method of multiplexed amplicon NGS library construction that meets this need.

SUMMARY

The present disclosure provides kits and methods for a targeted NGS library workflow comprising a multiplexed PCR for target amplification followed by an indexing PCR for incorporation of NGS adapter sequences. This workflow enables overlapping primer pairs in a single tube for contiguous coverage over target regions, while simultaneously preventing amplification of both primer dimers and undesirable mini-amplicons that result from overlapping primer pairs.

In some embodiments, a next generation sequencing (NGS) kit is provided that includes a first target-specific primer pair, a second target-specific primer pair, a universal primer that includes at least a portion of a universal sequence, a first indexing primer that includes a first indexing primer sequence and a first adaptor sequence, a second indexing primer that includes at least a portion of the universal sequence and a second adaptor sequence that is different from the first adaptor sequence, where the first target-specific primer pair includes a first target-specific primer that includes a first target-specific sequence that is complementary to a first target sequence on a substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence.

In some embodiments, a method for next generation sequencing library preparation is provided that includes combining a first target-specific primer pair, a second target-specific primer pair, a substrate nucleic acid molecule, deoxynucleoside triphosphates (dNTPs), a first DNA polymerase and a universal primer in a single reaction vessel to yield a first polymerase chain reaction (PCR) mixture, and subjecting the first PCR mixture to a series of PCR cycles under conditions sufficient to generate target-specific amplicons from the first target-specific primer pair and the second target-specific primer pair and amplify the target-specific amplicons from the universal primer, where the universal primer includes at least a portion of the universal sequence, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the method further includes purifying the target-specific amplicons from the first PCR mixture to yield a pre-indexing sample, combining the pre-indexing sample, a first indexing primer, a second indexing primer, dNTPs and a second DNA polymerase to yield a second PCR mixture, and subjecting the second PCR mixture to an additional series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence.

In some embodiments, a method for next generation sequencing library preparation is provided that includes combining a first target-specific primer pair, a second target-specific primer pair, a substrate nucleic acid molecule, deoxynucleoside triphosphates (dNTPs), and a first DNA polymerase in a single reaction vessel to yield a first polymerase chain reaction (PCR) mixture, and subjecting the first PCR mixture to a first series of PCR cycles under conditions sufficient to generate target-specific amplicons from the first target-specific primer pair and the second target-specific primer pair, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the target-specific amplicons can then be purified from the first PCR reaction mixture to yield a purified target-specific amplicon sample that can then be combined with a universal primer that includes at least a portion of the universal sequence and, optionally, dNTPs and a second DNA polymerase to yield a second PCR reaction mixture followed by subjecting the second PCR reaction mixture to a second series of PCR cycles under conditions sufficient to amplify the target-specific amplicons from the universal primer. In some embodiments, the method further includes purifying the target-specific amplicons from the second PCR mixture to yield a pre-indexing sample, combining the pre-indexing sample, a first indexing primer, a second indexing primer and, optionally, dNTPs and a third DNA polymerase to yield a third PCR mixture, and subjecting the third PCR mixture to a third series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence. In some embodiments, the second target-specific primer, the fourth target-specific primer or both can include a molecular identifier (MID) sequence.

BRIEF DESCRIPTION OF THE DRAWINGS

FIG. 7 discloses SEQ ID NOs 190, 191, 190, 192, 193, 191, 191, 190, 192, 193, 191, 191, 191, 193, 194, 191, 193, 194, 192, 193, 191, 194, 192 and 191, respectively, in order of appearance.

FIG. 8 discloses SEQ ID NOs 195, 191, 195, 192, 191, 195, 192, 191, 191, 196, 191, 197, 196, 197, 192, 196, 197 and 192, respectively, in order of appearance.

FIG. 9 depicts a specific embodiment where the universal sequence A is a portion of the P7 Illumina adapter, and the first indexing primer sequence T is a portion of the Illumina P5 adapter. This allows the remainder of the Illumina P5 adapter to be introduced by a P5 indexing primer in the first indexing PCR cycle, followed by annealing and extension of the P7 indexing primer on the P7 universal sequence in the second cycle. FIG. 9 discloses SEQ ID NOs 198, 199, 198, 200, 199, 200, 198, 199, 228, 230, 228, 231, 230, 231, 229, 230, 231 and 229, respectively, in order of appearance.

FIG. 14 depicts read lengths for the sequence data from Example 3. It is notable that there is not a significant number of short reads from primer dimers.

DETAILED DESCRIPTION OF THE INVENTION

Figure 1:
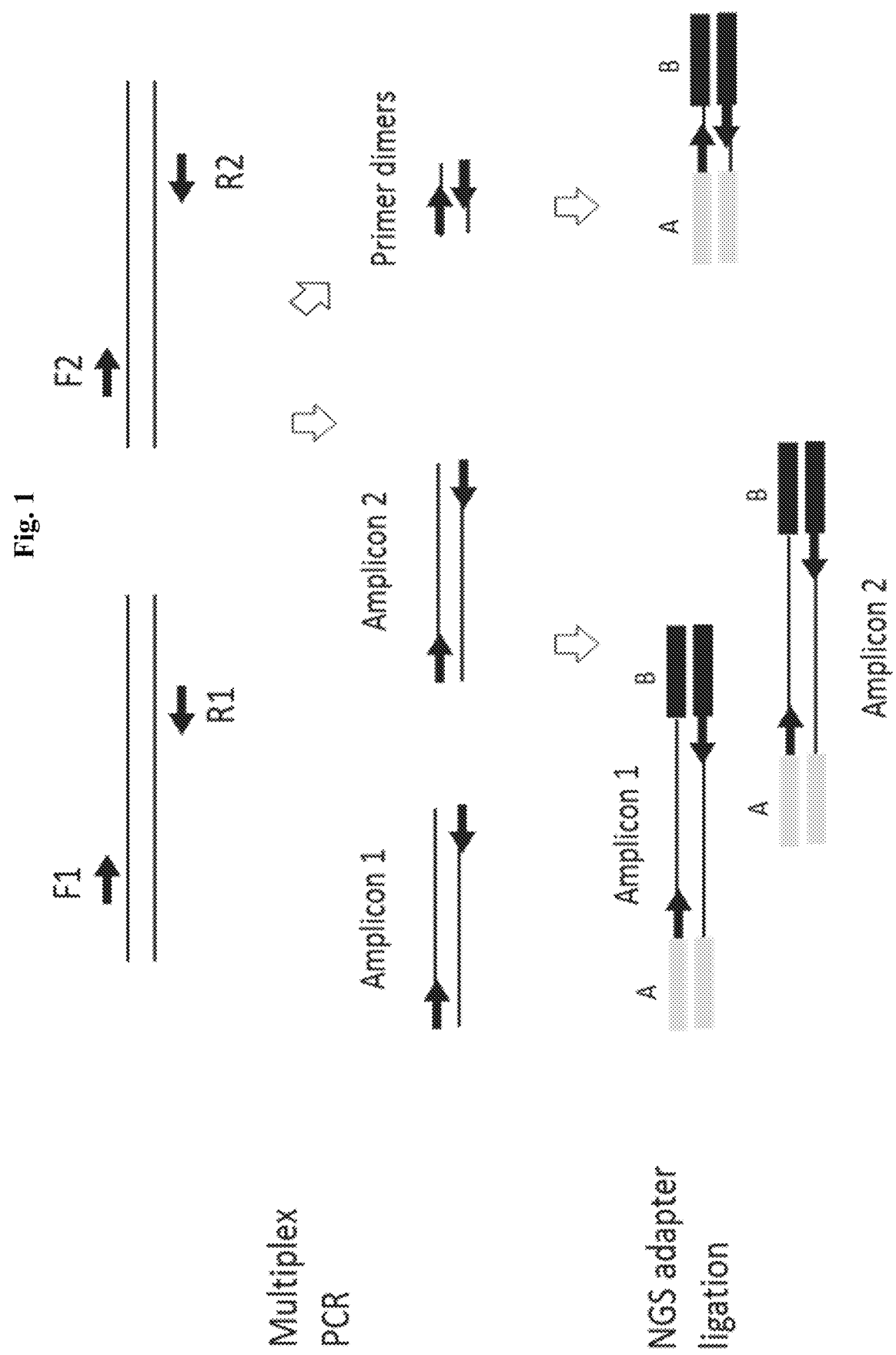
FIG. 1 depicts a basic method of targeted NGS library construction using multiplex PCR followed by adapter ligation.
Figure 2:
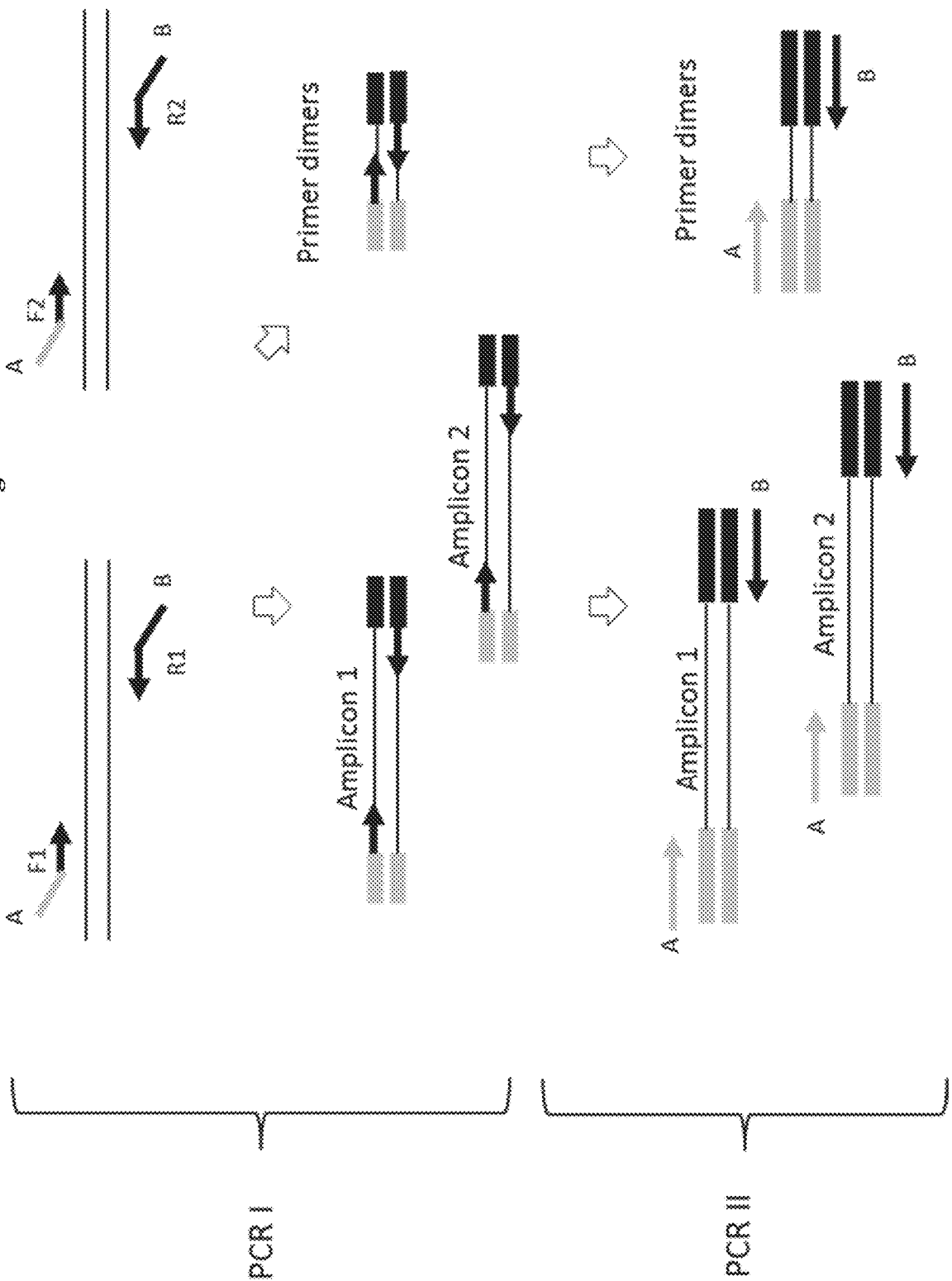
FIG. 2 depicts a basic method of targeted NGS library construction using multiplex PCR with primers that introduce a partial NGS adapter sequence A and B, where completion of the library occurs with a second PCR using indexing primers.

The present disclosure provides compositions, including kits, and methods for the preparation of next generation sequencing libraries using multiplex PCR.

Definitions

Certain terminology is used in the following description for convenience only and is not limiting. Unless specifically set forth herein, the terms "a," "an," and "the" are not limited to one element, but instead should be read consistent with the meaning of "one or more," "at least one," and "one or more than one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about," when used with a numerical value, is intended to include +/−10%. For example, if a number of nucleotides is identified as about 200, this would include 180 to 200 (plus or minus 10%).

Unless otherwise defined, all technical and scientific terms used herein have the same meaning as commonly understood by one of ordinary skill in the art.

A "target-specific primer pair" as used herein can be understood to include a first primer and a second primer that each have sequences complementary to a substrate nucleic acid molecule and which, as a pair, are sufficient to amplify a target region of the substrate nucleic acid molecule under PCR reaction conditions. For example, a target-specific primer pair can include a forward primer and a reverse primer, as commonly understood in the art.

In some embodiments, a next generation sequencing (NGS) kit is provided that includes a first target-specific primer pair, a second target-specific primer pair, a universal primer that includes at least a portion of a universal sequence, a first indexing primer that includes a first indexing primer sequence and a first adaptor sequence, a second indexing primer that includes at least a portion of the universal sequence and a second adaptor sequence that is different from the first adaptor sequence, where the first target-specific primer pair includes a first target-specific primer that includes a first target-specific sequence that is complementary to a first target sequence on a substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence.

In some embodiments, a method for next generation sequencing library preparation is provided that includes combining a first target-specific primer pair, a second target-specific primer pair, a substrate nucleic acid molecule, deoxynucleoside triphosphates (dNTPs), a first DNA polymerase and a universal primer in a single reaction vessel to yield a first polymerase chain reaction (PCR) mixture, and subjecting the first PCR mixture to a series of PCR cycles under conditions sufficient to generate target-specific amplicons from the first target-specific primer pair and the second target-specific primer pair and amplify the target-specific amplicons from the universal primer, where the universal primer includes at least a portion of the universal sequence, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the method further includes purifying the target-specific amplicons from the first PCR mixture to yield a pre-indexing sample, combining the pre-indexing sample, a first indexing primer, a second indexing primer, dNTPs and a second DNA polymerase to yield a second PCR mixture, and subjecting the second PCR mixture to an additional series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence.

In some embodiments, a method for next generation sequencing library preparation is provided that includes combining a first target-specific primer pair, a second target-specific primer pair, a substrate nucleic acid molecule, deoxynucleoside triphosphates (dNTPs), and a first DNA polymerase in a single reaction vessel to yield a first polymerase chain reaction (PCR) mixture, and subjecting the first PCR mixture to a first series of PCR cycles under conditions sufficient to generate target-specific amplicons from the first target-specific primer pair and the second target-specific primer pair, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the target-specific amplicons can then be purified from the first PCR reaction mixture to yield a purified target-specific amplicon sample that can then be combined with a universal primer that includes at least a portion of the universal sequence and, optionally, dNTPs and a second DNA polymerase to yield a second PCR reaction mixture followed by subjecting the second PCR reaction mixture to a second series of PCR cycles under conditions sufficient to amplify the target-specific amplicons from the universal primer. In some embodiments, the method further includes purifying the target-specific amplicons from the second PCR mixture to yield a pre-indexing sample, combining the pre-indexing sample, a first indexing primer, a second indexing primer and, optionally, dNTPs and a third DNA polymerase to yield a third PCR mixture, and subjecting the third PCR mixture to a third series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence. In some embodiments, the second target-specific primer, the fourth target-specific primer or both can include a molecular identifier (MID) sequence.

Target-Specific Primers and Primer Pairs

Target-Specific Primer Pairs

The target-specific primer pairs of the present disclosure each include two target-specific primers, a first target-specific primer and a second target-specific primer, for amplifying a target region of a substrate nucleic acid molecule in a PCR reaction. In some embodiments, two or more target-specific primer pairs can be designed with sequences sufficient to amplify overlapping regions of the substrate nucleic acid molecule in a PCR reaction. By way of example, but not limitation, kits or methods of the present can comprise or use a plurality of target-specific primer pairs in which two or more of the target-specific primer pairs can be designed with sequences sufficient to amplify overlapping regions of the substrate nucleic acid molecule in a PCR reaction. It should be understood that the target-specific sequences of each target-specific primer pair are different between target-specific primer pairs and can be different between the first and second target-specific primers. In some embodiments, two target-specific primer pairs are used in method or included in kits of the present disclosure, the two target-specific primers, respectively the first and second target-specific primer pairs, include a first target-specific primer and a second target-specific primer, and a third target-specific primer and a fourth target-specific primer, respectively.

Target-Specific Primers

In some embodiments, the first target-specific primer of each target-specific primer pair can include a target-specific sequence, a first indexing primer sequence and a universal sequence. In some embodiments, the second target-specific primer of each target-specific primer pair can include a target-specific sequence and the universal sequence, where the target-specific sequence of the second target-specific primer is different from the target-specific sequence of the first target-specific primer. It should be understood that the "first target-specific primer" and the "second target-specific primer" can refer to the forward primer and reverse primer, respectively, or vice versa. The same applies to the "third target-specific primer" and the "fourth target-specific primer" as referred to herein, which are the primer pair for the second target-specific primer pair. In some embodiments, the target-specific sequence of each of the first and second target-specific primers is located at a 3' terminus of the target-specific primer. In some embodiments, the first target-specific primer includes, in a 5' to 3' direction, a universal sequence, a first indexing primer sequence and a target-specific sequence. In some embodiments, the second target-specific primer includes, in a 5' to 3' direction, the universal primer sequence and a target-specific sequence.

In some embodiments, the second target-specific primer, the fourth target-specific primer or both can include a molecular identifier (MID) sequence. In some embodiments, the MID sequence can be positioned between the target-specific sequence and the universal sequence of the target-specific primer. By way of example, but not limitation, the second target-specific primer can include a first MID sequence that is positioned between the second target-specific sequence and the universal sequence. By way of further example, but not limitation, the fourth target-specific primer can include a second MID sequence that is positioned between the fourth target-specific sequence and the universal sequence. In some embodiments, the first MID sequence and the second MID sequence can be the same or different. In some embodiments, the MID sequence can include from about 5 to about 15 nucleotides. By way of example, but not limitation, the MID sequence can include from about 5 to about 10, about 10 to about 15, at least 5, at least 10, 5, 6, 7, 8 9, 10, 11, 12, 13, 14 or 15 nucleotides.

In some embodiments, the target-specific primers of the present disclosure can have a melting temperature ($T_m$) of between about 56° C. to about 72° C., preferably between about 62° C. to about 66° C. By way of example, but not limitation, the melting temperature ($T_m$) of the target-specific primers of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C. Melting temperatures for nucleic acid molecules can be determined by methods known to those of skill in the art included the use of software to calculate expected melting temperature for a particular pairing of nucleic acid molecules.

Target-Specific Sequences

The target-specific primers of the present disclosure can include a target-specific sequence. The target-specific sequence can be complementary to a target sequence on a substrate nucleic acid molecule.

In some embodiments, the target-specific sequence of each target-specific primer can include from about 15 to about 40 nucleotides. By way of example, but not limitation, the target-specific sequence of each target-specific primer can include from about 15 to about 40 nucleotides, about 15 to about 30 nucleotides, about 15 to about 20 nucleotides, about 20 to about 30 nucleotides, about 18 to about 36 nucleotides, about 15 nucleotides, about 20 nucleotides, about 25 nucleotides, about 30 nucleotides, about 35 nucleotides, about 40 nucleotides, at least 5 nucleotides, at least 10 nucleotides, at least 15 nucleotides, at least 20 nucleotides, at least 30 nucleotides, or at least 35 nucleotides.

In some embodiments, the target-specific sequences can each have a melting temperature ($T_m$) of between about 56° C. to about 72° C., preferably between about 62° C. to about 66° C. By way of example, but not limitation, the melting temperature ($T_m$) of the target-specific sequences of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C. By way of example but not limitation, the target-specific sequences can have a $T_m$ between about 56° C. to about 72° C. can include about 18 to about 36 nucleotides. Target-specific sequences can be shorter for more GC-rich target sequences while longer target-specific sequences can be used for more AT-rich target sequences, but as short as possible to keep short primer dimer and mini-amplicon size to a minimum (to facilitate selective amplification) and to reduce oligonucleotide synthesis cost. Target-specific sequences can also be designed to be of sufficient nucleotide complexity and uniqueness (do not contain repetitive or common sequence motifs) to confer high specificity during priming and amplification to avoid off-target amplification that increases the cost of sequencing.

First Indexing Primer Sequence

In some embodiments, the first target-specific primer of each primer pair can include a first indexing primer sequence. In some embodiments, the first target-specific primer of each primer pair can include a first indexing primer sequence and the second target-specific primer of each primer pair does not include the first indexing primer sequence. In some embodiments, the first indexing primer sequence is positioned 5' to the target-specific sequence of the first target-specific primer.

In some embodiments, the first indexing primer sequence can include from about 4 to about 40 nucleotides. By way of example, but not limitation, the first indexing primer sequence can include from about 5 to about 40 nucleotides, about 5 to about 30 nucleotides, about 5 to about 20 nucleotides, about 5 to about 10 nucleotides, about 6 to about 20 nucleotides, about 10 to about 40 nucleotides, about 20 to about 40 nucleotides, about 30 to about 40 nucleotides, about 10 to about 30 nucleotides, about 20 to about 30 nucleotides, about 10 nucleotides, about 15 nucleotides, about 20 nucleotides, about 25 nucleotides, about 30 nucleotides, about 35 nucleotides, about 40 nucleotides, at least 5 nucleotides, at least 10 nucleotides, at least 15 nucleotides, at least 20 nucleotides, at least 30 nucleotides, or at least 35 nucleotides.

In some embodiments, the first indexing primer sequence can each have a melting temperature ($T_m$) of between about 56° C. to about 72° C., preferably between about 62° C. to about 66° C. By way of example, but not limitation, the melting temperature ($T_m$) of the first indexing primer sequence of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C. By way of example but not limitation, the first indexing primer sequence can have a $T_m$ between about 56° C. to about 72° C. and can include about 4 to about 40 nucleotides. Shorter first indexing primer sequences are preferred to keep primer dimer and mini-amplicon size to a minimum (to facilitate selective amplification) and to reduce oligonucleotide synthesis cost. When using a synthetic sequence, GC-rich designs can enable shorter length to achieve the desired $T_m$. The synthetic sequence is unique and differs from the target and NGS adapter sequences. Alternatively, the first indexing primer sequence can be a portion of an NGS adapter sequence, such as truncated Illumina TruSeq P5 and P7 adapters, or a portion of an Ion Torrent A or P1 adapter, or others.

In some embodiments, the first indexing primer sequence constitutes a portion of the first adaptor sequence. In some embodiments, the first indexing primer sequence is not complementary to any sequence of the substrate nucleic acid molecule. In some embodiments, the first indexing primer sequence does not form any portion of the first adaptor sequence.

In some embodiments, the first indexing primer sequence can consist of cytosine bases, guanine bases or a combination thereof.

Universal Sequence

In some embodiments, the universal sequence can include from about 8 to about 48 nucleotides. By way of example, but not limitation, the universal sequence can include from about 8 to about 40, about 8 to about 30, about 8 to about 20, about 8 to about 15, about 15 to about 48, about 20 to about 48, about 25 to about 48, about 30 to about 48, about 35 to about 48, about 40 to about 48, about 10, about 15, about 20, about 30, about 40, at least 10, at least 20, at least 30, or at least 40 nucleotides. By way of further example, but not limitation, the universal sequence can comprise from 5-40 nucleotides, 20-40 nucleotides, 30-40 nucleotides, 10-30 nucleotides, 20-30 nucleotides, about 10 nucleotides, about 15 nucleotides, about 20 nucleotides, about 25 nucleotides, about 30 nucleotides, about 35 nucleotides, about 40 nucleotides, at least 5 nucleotides, at least 10 nucleotides, at least 15 nucleotides, at least 20 nucleotides, at least 25 nucleotides, at least 30 nucleotides, or at least 35 nucleotides. In some embodiments, the universal sequence can have a melting temperature ($T_m$) of between about 56° C. to about 72° C., preferably between about 62° C. to about 66° C. By way of example, but not limitation, the melting temperature ($T_m$) of the universal sequence of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C. By way of example but not limitation, the universal sequence can have a $T_m$ between about 56° C. to about 72° C. and can include about 8 to about 48 nucleotides. It should be understood that the combined $T_m$ and primer concentration enable permissive priming of intended amplicon and super-amplicon secondary structure formed by self-complementary universal tail sequences, where the combined $T_m$ and primer concentration are restriction to priming the more stable secondary structure of the shorter primer dimers and mini-amplicons.

In some embodiments, the universal sequence consists of cytosine bases, guanine bases, or a combination of both. The use of the shortest sequence possible can keep primer dimer and mini-amplicon size to a minimum (to facilitate selective amplification) and reduces oligo synthesis cost. When using a synthetic sequence, GC-rich designs enable shorter length to achieve the desired $T_m$. The synthetic sequence is unique and differs from the target sequences, the first indexing primer sequence and NGS adapter sequences. Alternatively, the universal primer sequence can be a portion of an NGS adapter sequence, such as, by way of example but not limitation, truncated Illumina TruSeq P5 and P7 adapters, or a portion of an Ion Torrent A or P1 adapter, or others. In some embodiments, the universal sequence can constitute a portion of a second adaptor sequence.

Universal Primer

In some embodiments, the universal primer comprises at least a portion of the universal sequence. In some embodiments, the universal primer comprises the universal sequence.

The universal primer is designed to include at least a portion of the universal sequence incorporated on the target-specific primers. A design that is shorter than the universal sequence incorporated on the target-specific primer increases the stringency of amplification by increasing the competition between self-complementary secondary structure versus primer annealing. A design that is longer than the universal sequence incorporated on the target-specific primer also increases the stringency of amplification by increasing the length and stability of the self-complementary duplex once the longer sequence is incorporated. In some embodiments, the universal primer can include from about 10 to about 70 nucleotides. By way of example, but not limitation, the universal primer can include from about 10 to about 60, about 10 to about 50, about 20 to about 40, about 30, about 20 to about 770, about 30 to about 70, about 40 to about 70, about 50 to about 70, about 60 to about 70, about 30, about 40, about 50, about 60, about 70, at least 10, at least 15, at least 20, at least 30, at least 40, at least 50, or at least 60 nucleotides.

In some embodiments, the universal primer can have a melting temperature ($T_m$) of between about 56° C. to about 72° C., preferably between about 62° C. to about 66° C. By way of example, but not limitation, the melting temperature ($T_m$) of the universal primer of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C.

First Indexing Primer

In some embodiments, the first indexing primer can include at least a portion of the first indexing primer sequence and a first adaptor sequence. In some embodiments, the first indexing primer includes the first indexing primer sequence.

The 3' terminus of the first indexing primer can be designed to include all or a portion of the first indexing primer sequence length introduced by either the forward or reverse target-specific primer of each primer pair. The 5' tail of the first indexing primers can include the length and composition of the platform-specific adapter sequence such as Illumina TruSeq P5 and P7 with sample-specific indexes, Ion Torrent adapters A and P1 with sample-specific barcodes, and others. In the case where the first indexing primer sequence is a portion of the first NGS adapter, the 5' tail of the first indexing primer is the remainder of the first adapter sequence. In the case where the first indexing primer sequence is a synthetic sequence that is different from the target sequence and the NGS adapter sequence, the 5' tail of the first indexing primer is the entire first NGS adapter sequence. The sample specific index sequences or barcodes can be 6 to 8 nucleotides or longer in length and can be custom index or barcode sequences or sequences provided and validated by the sequencing platform provider. In some embodiments, the first indexing primer can include from about 5 to about 100 nucleotides. By way of example but not limitation, the first indexing primer can include from about 10 to about 100, about 20 to about 100, about 30 to about 100, about 40 to about 100, about 50 to about 100, about 60 to about 100, about 70 to about 100, about 80 to about 100, about 90 to about 100, about 20 to about 90, about 20 to about 80, about 30 to about 90, about 30 to about 80, about 40 to about 90, about 40 to about 80, about 50 to about 90, about 50 to about 80, about 60 to about 90, about 60 to about 80, about 10, about 20, about 30, about 40, about 50, about 60, about 70, about 80, about 90, about 100, at least 5, at least 10, at least 15, at least 20, at least 25, at least 30, at least 40, at least 50, at least 60, at least 70, at least 80 or at least 90 nucleotides. In some embodiments, the first indexing primer can have a melting temperature ($T_m$) of between about 56° C. to about 72° C., preferably between about 62° C. to about 66° C. By way of example, but not limitation, the melting temperature ($T_m$) of the first indexing primer of the present disclosure can be about 56° C., 57° C., 58° C., 59° C., 60° C., 61° C., 62° C., 63° C., 64° C., 65° C., 66° C., 67° C., 68° C., 69° C., 70° C., 71° C. or 72° C. It should be understood that reference to a melting temperature is to the melting temperature of the recited element in the relevant PCR step where the recited element anneals and is able to extend to produce an amplicon.

Second Indexing Primer

In some embodiments, the second indexing primer can include at least a portion of the universal sequence and a second adaptor sequence. In some embodiments, the second indexing primer does not include the first indexing primer sequence. In some embodiments, the second adaptor sequence is different from the first adaptor sequence. In some embodiments, the second indexing primer can include the universal sequence and a second adaptor sequence.

The 3' terminus of the second indexing primer can be designed to include all or a portion of the universal sequence length introduced by both the forward or reverse target-specific primer of each primer pair. The 5' tail of the second indexing primers correspond to the length and composition of the platform-specific adapter sequence such as Illumina TruSeq P5 and P7 with sample-specific indexes, Ion Torrent adapters A and P1 with sample-specific barcodes, and others. The second indexing primer can include at least a portion of the second NGS adapter that was not introduced by the first indexing primer. There is no required order of which adapter is incorporated first. In the case where the universal sequence is a portion of the second NGS adapter, the 5' tail of the second indexing primer is the remainder of the second adapter sequence. In the case where the universal sequence is a synthetic sequence that is different from the target sequence, the first indexing primer sequence and the second NGS adapter sequence, the 5' tail of the second indexing primer is the entire second NGS adapter sequence. The sample-specific index sequences or barcodes can be 6 to 8 nucleotides or longer in length and can be custom index or barcode sequences or sequences provided and validated by the sequencing platform provider. In some embodiments, the second indexing primer can include from about 5 to about 100 nucleotides. By way of example but not limitation, the second indexing primer can include from about 10 to about 100, about 20 to about 100, about 30 to about 100, about 40 to about 100, about 50 to about 100, about 60 to about 100, about 70 to about 100, about 80 to about 100, about 90 to about 100, about 20 to about 90, about 20 to about 80, about 30 to about 90, about 30 to about 80, about 40 to about 90, about 40 to about 80, about 50 to about 90, about 50 to about 80, about 60 to about 90, about 60 to about 80, about 10, about 20, about 30, about 40, about 50, about 60, about 70, about 80, about 90, about 100, at least 5, at least 10, at least 15, at least 20, at least 25, at least 30, at least 40, at least 50, at least 60, at least 70, at least 80 or at least 90 nucleotides. In some embodiments, the first indexing primer and the second indexing primer have different nucleotide lengths. By way of example, but not limitation, the second indexing primer can be shorter than the first indexing primer, or vice versa.

Amplicon Length and Degree of Overlap

In considering amplicon length, the most important product length is the amplicon produced by the target-specific primers, because selective amplification of this product by the universal primer is size dependent: the longer intended amplicons and super-amplicons amplify efficiently vs. the shorter primer dimers and mini-amplicons that do not. For the product of target-specific primers, the size of two portions of the amplicon are important for consideration: the length of the self-complementary dsDNA duplex formed by the universal sequence present at the termini of each amplicon that form ssDNA secondary structure after denaturation, and the length of the intervening region between the universal sequence that remains ssDNA. The length of the universal sequence has already been described above. The length of the ssDNA intervening region depends on the length of the target-specific primer sequences, the target sequence between the primers (ie the amplicon), the first indexing primer sequence, and optionally a molecular identifier (MID) sequence. In order to have optimal selective amplification where longer intended amplicons and super-amplicons are readily amplified by the universal primer and the shorter mini-amplicons and primer dimers are not, the length of the ssDNA intervening region should have a minimum of 70 bp to a maximum of 600 bp or more for short read sequencing platforms and 70 bp to 10 Kb or more for long read sequencing platforms. Designs that produce an intervening sequence less than 70 bp would be subject to inefficient amplification similar to shorter primer dimers and mini-amplicons. Similarly, in considering mini-amplicon size for selective amplification, the region of overlap between two primer pairs should be limited to 100 bp or less in order to ensure that these products are short enough to comprise stable secondary structure so they do not amplify efficiently. By way of example but not limitation, the overlap between primer pairs can be less than 100 nucleotides, 90 nucleotides, 80 nucleotides, 70 nucleotides, 60 nucleotides, 50 nucleotides, 40 nucleotides, 30 nucleotide, 20 nucleotides, 10 nucleotides or 5 nucleotides. Similarly, by way of example but not limitation, the overlap between primer pairs can be at least 1 nucleotide, 5 nucleotides, 10 nucleotides, 20 nucleotides, 30 nucleotides, 40 nucleotides, 50 nucleotides, 60 nucleotides, 70 nucleotides, 80 nucleotides or 90 nucleotides or any range or length between these values.

A second, unrelated consideration for ssDNA intervening region length is the type of target nucleic acid being used for target amplification. In the case of high quality, high molecular weight genomic DNA samples, the amplicon size is flexible and these substrates can support the range of possible sizes up to 600 bp or more for short read sequencing platforms and up to 10 Kb or more for long read sequencing platforms. In the case of formalin fixed paraffin embedded samples that are cross-linked and damaged, as well as cell-free DNA derived from blood plasma and fluids from other anatomical compartments (eg bronchial lavage, sputum, urine, endometrial lavage, peritoneal fluid, cerebrospinal fluid etc), amplicon length should be limited to 165 bp or less, where 100-150 bp is preferred to increase sensitivity of detection by increasing the likelihood that both primers of a pair are present on the majority of short fragments. By way of example but not limitation, the length of the amplicon between the universal sequences can be from about 70 nucleotides to about 10,000 nucleotides. By way of example, but not limitation, the length of the amplicon between the universal sequence can be from about 70 to about 5,000, about 70 to about 2,500, about 70 to about 1,000, about 70 to about 500, about 500 to about 10,000, about 500 to about 5,000, about 500 to about 2,500, about 500 to about 1,000, about 1,000 to about 10,000, about 1,000 to about 5,000, about 1,000 to about 2,500, about 2,500 to about 5,000, about 2,500 to about 5,000, about 5,000 to about 10,000, about 100, 110, 120, 130 140, 150, 160, 200, 500, 1,000, 2,000, 5,000, 10,000, at least 70, 80, 90, 100, 250, 500, 1,000, 2,500, 5,000 or 10,000 nucleotides and any valid range thereof or value within those values.

Multiplex PCR Methods

"Two-Step" PCR Method

In some embodiments, a method for next generation sequencing library preparation is provided that includes combining a first target-specific primer pair, a second target-specific primer pair, a substrate nucleic acid molecule, deoxynucleoside triphosphates (dNTPs), a first DNA polymerase and a universal primer in a single reaction vessel to yield a first polymerase chain reaction (PCR) mixture, and subjecting the first PCR mixture to a series of PCR cycles under conditions sufficient to generate target-specific amplicons from the first target-specific primer pair and the second target-specific primer pair and amplify the target-specific amplicons from the universal primer, where the universal primer includes at least a portion of the universal sequence, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the method further includes purifying the target-specific amplicons from the first PCR mixture to yield a pre-indexing sample, combining the pre-indexing sample, a first indexing primer, a second indexing primer, dNTPs and a second DNA polymerase to yield a second PCR mixture, and subjecting the second PCR mixture to an additional series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence.

Figure 4:
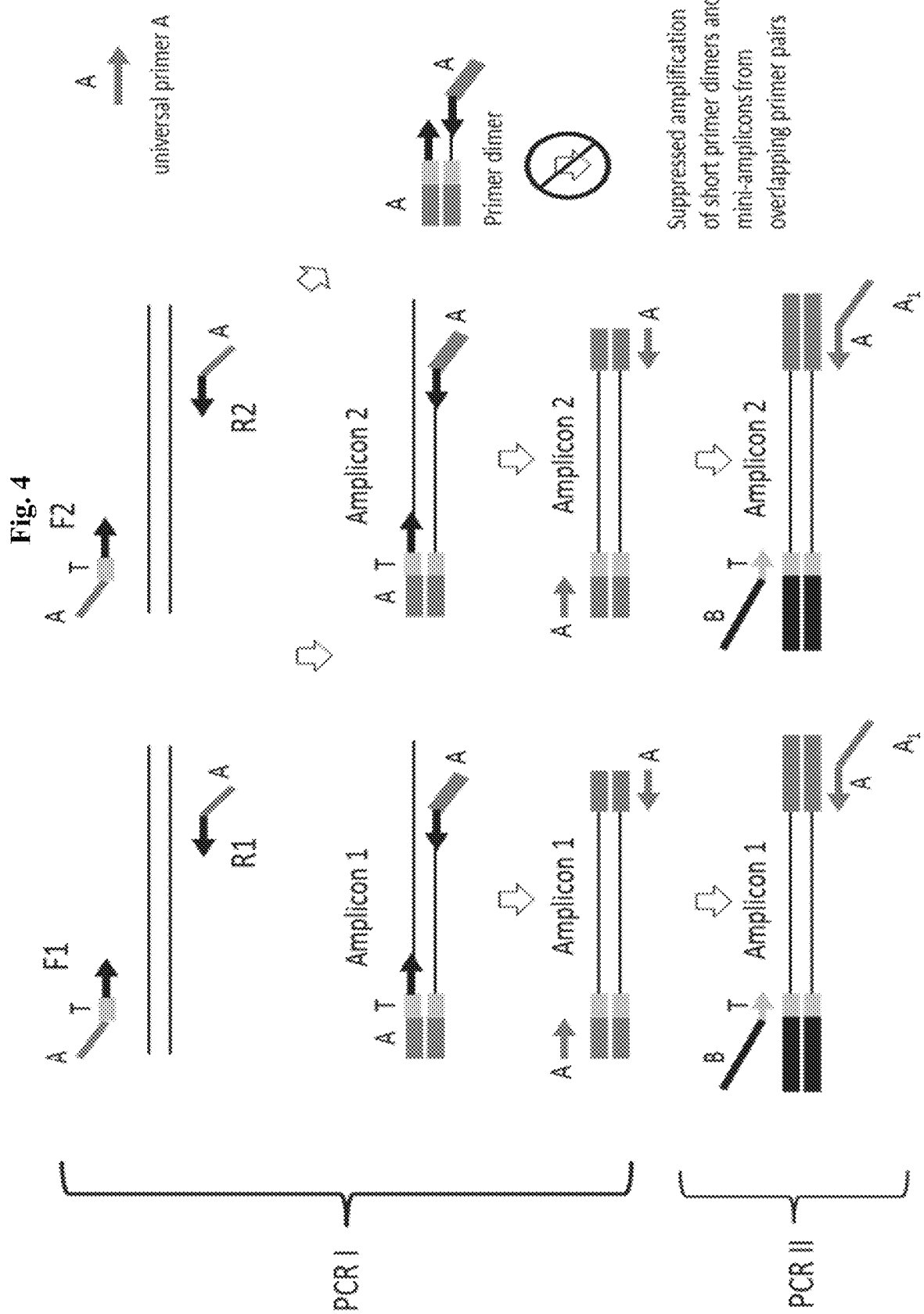
FIG. 4 depicts a method of the present disclosure of multiplexed PCR using overlapping primer pairs that can prevent amplification of the undesired mini-amplicon as well as primer dimers.

In the two-step PCR method, two PCR steps are performed: a multiplex PCR target enrichment step that uniquely introduces annealing sequences for subsequent incorporation of each NGS adapter on target-specific primers, which includes a universal primer for target amplification, followed by a purification step or unusued primer digestion step. Then a second indexing PCR step completes incorporation of the NGS adapter sequences through annealing to the sequences introduced during the first PCR, and additionally introduces sample specific index sequences that are required for multiplexed sequencing (FIG. 4).

"Three-Step" PCR Method

In some embodiments, a method for next generation sequencing library preparation is provided that includes combining a first target-specific primer pair, a second target-specific primer pair, a substrate nucleic acid molecule, deoxynucleoside triphosphates (dNTPs), and a first DNA polymerase in a single reaction vessel to yield a first polymerase chain reaction (PCR) mixture, and subjecting the first PCR mixture to a first series of PCR cycles under conditions sufficient to generate target-specific amplicons from the first target-specific primer pair and the second target-specific primer pair, where the first target-specific primer pair includes a first target-specific primer that includes a first target-specific sequence that is complementary to a first target sequence on the substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the target-specific amplicons can then be purified from the first PCR reaction mixture to yield a purified target-specific amplicon sample that can then be combined with a universal primer that includes at least a portion of the universal sequence and, optionally, dNTPs and a second DNA polymerase to yield a second PCR reaction mixture followed by subjecting the second PCR reaction mixture to a second series of PCR cycles under conditions sufficient to amplify the target-specific amplicons from the universal primer. In some embodiments, the method further includes purifying the target-specific amplicons from the second PCR mixture to yield a pre-indexing sample, combining the pre-indexing sample, a first indexing primer, a second indexing primer and, optionally, dNTPs and a third DNA polymerase to yield a third PCR mixture, and subjecting the third PCR mixture to a third series of PCR cycles under conditions sufficient to generate asymmetrical amplicons from the first indexing primer and the second indexing primer, where the first indexing primer includes at least a portion of the first indexing primer sequence and a first adaptor sequence, and where the second indexing primer includes at least a portion of the universal sequence and a second adaptor sequence. In some embodiments, the second target-specific primer, the fourth target-specific primer or both can include a molecular identifier (MID) sequence.

Figure 5:
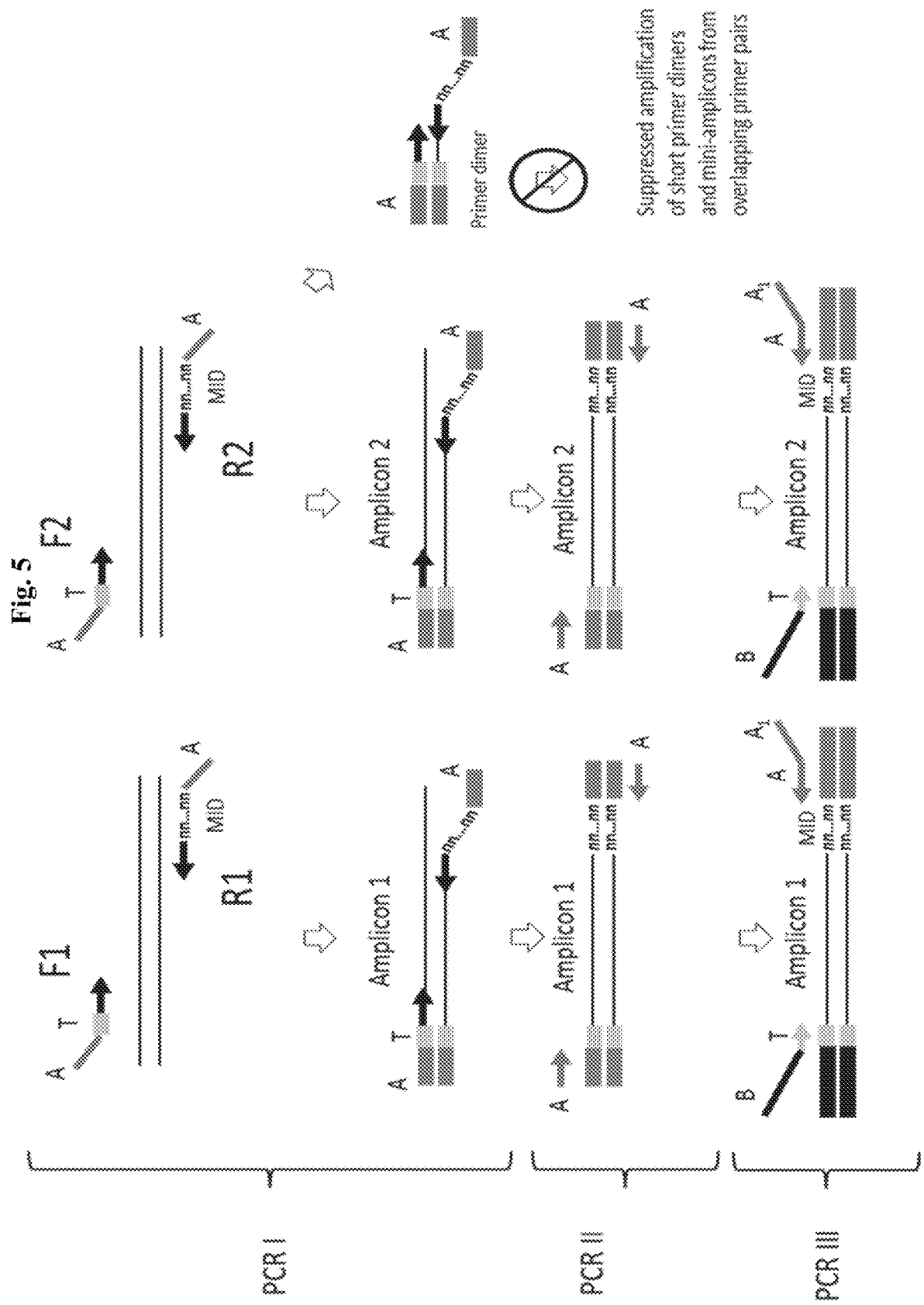
FIG. 5 depicts an alternative method of the present disclosure of multiplexed PCR that introduces MIDs (molecular identifiers) and can prevent primer dimers and undesired mini-amplicons from dominating the reaction.

In the "three-step" PCR method, MID sequences can be incorporated, if desired, by using three PCR steps instead of 2 as shown in FIG. 5. During the first PCR, MID (molecular identifier) incorporation can limited to 2 to 3 or more PCR cycles using the target specific primers comprising molecular identifiers of 5 or more N bases, followed by a purification or digestion step to remove unused primers comprising molecular identifiers. Then a second PCR is performed using a universal primer for target amplification, which is followed by a purification or digestion step and then a third PCR using indexing primers to complete NGS library construction. Alternatively, the "three-step" PCR method can be used without molecular identifiers which separates the target-specific primer amplification and the universal primer amplification steps.

In the foregoing "two-step" and "three-step" PCR method, pairs of target-specific primers are designed to desired target loci, whereby both primers of each pair have an identical 5' universal sequence that includes a truncated NGS adapter sequence or a unique, synthetic sequence that does not correspond to either a target or an NGS adapter sequence (sequence $A_1$ or the combination of a portion or all of A and $A_1$ if the universal sequence includes a portion of the NGS adapter sequence in FIGS. 4 and 5). In addition, an asymmetry in primer design is introduced, where one primer of each pair also comprises a first indexing primer sequence (sequence T in FIGS. 4 and 5) that is located 3' to the 5' universal sequence and comprises a truncated first NGS adapter sequence or a unique, synthetic sequence that does not correspond to either the target specific sequence or an NGS adapter sequence and is different from the universal sequence A, and that is positioned 5' to the target specific portion of the primer. In other words, the first indexing primer sequence is not the same as the universal sequence A and is different from the target-binding portion of the primer. If unique molecular identifiers are desired, the opposite primer of each pair that does not contain the first indexing primer sequence instead comprises a molecular identifier (MID) sequence that is a stretch of 5-15 random N bases of a defined length (the nn . . . nn sequence in FIG. 5), depending on the complexity of molecular tag sequences desired.

For each asymmetric primer pair, the first indexing primer sequence can be located on either the forward target specific primer or the reverse target specific primer. It is not necessary to alter the orientation of the asymmetric primer pair compositions along a contiguous tiled design of overlapping primer pairs. The asymmetric primer pairs of the instant invention can be in a consistent orientation, an alternating orientation or a random orientation with regard to adjacent, overlapping primer pairs. Similarly, there is no requirement for the molecular identifier sequence to be in any specific orientation for one asymmetric primer pair relative to adjacent primer pairs along a contiguous tiled design of overlapping primer pairs.

In alternative embodiments, both the first indexing primer sequence and molecular identifier sequence could be positioned adjacently on one primer of each pair, where the molecular identifier is positioned 3' to the first indexing primer sequence, although such an asymmetric composition is less desirable due to the significant increase in primer length for one primer of each pair. Similarly, the orientation of such asymmetric primer pairs would not need to be alternated along a contiguous tiled design of overlapping primer pairs: they could have a consistent orientation, an alternating orientation or a random orientation relative to adjacent primer pairs.

The first target-specific PCR cycles can have elongated cycling times to allow the high complexity of asymmetric primer pairs, each of which is at a low concentration, to create universal and first indexing primer tagged asymmetric amplicons from their target sequences (sequence A and T, respectively, FIGS. 4 and 5). If molecular identifier sequences are used, the elongated multiplex PCR cycles can be limited to 2 to 3 in order to avoid incorporation of additional molecular identifier sequences over copies of previously generated amplicons, where a purification or digestion step is also required to remove unused molecular identifier containing primers; if molecular identifier sequences are not used, the elongated multiplex PCR cycles can be performed for more than 2 to 3 cycles, where 4 or more elongated cycles is sufficient.

Following the elongated multiplex cycles (2, 3, 4 or more), PCR can be continued with shorter elongation times for a second phase of amplification that uses the single, universal primer A that includes at least a portion of the universal sequence A flanking each target-specific asymmetric amplicon (FIGS. 4 and 5). The universal primer can be used at a relatively high concentration compared to the target-specific primers (e.g., 1 uM to 10 uM or more), where the total number of cycles is determined by the desired product yield. The concentration of target-specific primers is not sufficient to amplify the target amplicons to the desired product yield, so the universal primer takes over the amplification reaction with minimal additional primer dimer formation from target-specific priming. Additionally, the primer dimers that accumulate will be shorter in length than the desired amplicons and will be subject to stable secondary structure at the annealing temperature due to the self-complementarity of the universal sequence A, which results in less efficient amplification by the single universal primer, whereas the larger intended amplicons and super amplicons have a less stable secondary structure and annealing and amplification by the universal primer readily occurs. If molecular identifier sequences are used, a purification step or exonuclease I digestion of unused multiplex primers can be performed prior to addition of the universal primer, in order to prevent additional molecular identifier sequences labeling subsequent copies of previously generated amplicons. If molecular identifier sequences are not used, the universal primer can be added at the beginning of the reaction with the multiplexed target-specific primers and will become functional once universal adapter tagged asymmetric amplicons are generated. Each asymmetric amplicon is comprised of a target specific sequence selected by each primer pair, a universal sequence at both ends of the amplicon, and a first indexing primer sequence T positioned on one side internal to the universal sequence A, and optionally a molecular identifier at the opposite or same end as the first indexing primer sequence. During these steps, neither the first indexing primer sequence nor the molecular identifier play any role in enrichment of desired amplicons over undesired amplicons (primer dimers and short amplicons that result from overlapping primer pairs). Both sequence elements are inert during target-specific and universal PCR cycles and are only important for the second indexing PCR step that completes NGS library construction.

In an alternative embodiment, MIDs are split and a portion is placed on each primer of a pair, directly 5' of the target-specific portion. In this example, the target-specific cycles can be limited to 2 to 3, followed by a purification or exonuclease I digestion step, or additional cycles can be performed where detailed tracking of progeny priming events that override the original molecular identifiers is performed, albeit a more complex bioinformatics analysis is required over categorizing based on the number of unique amplicons created initially.

Figure 6:
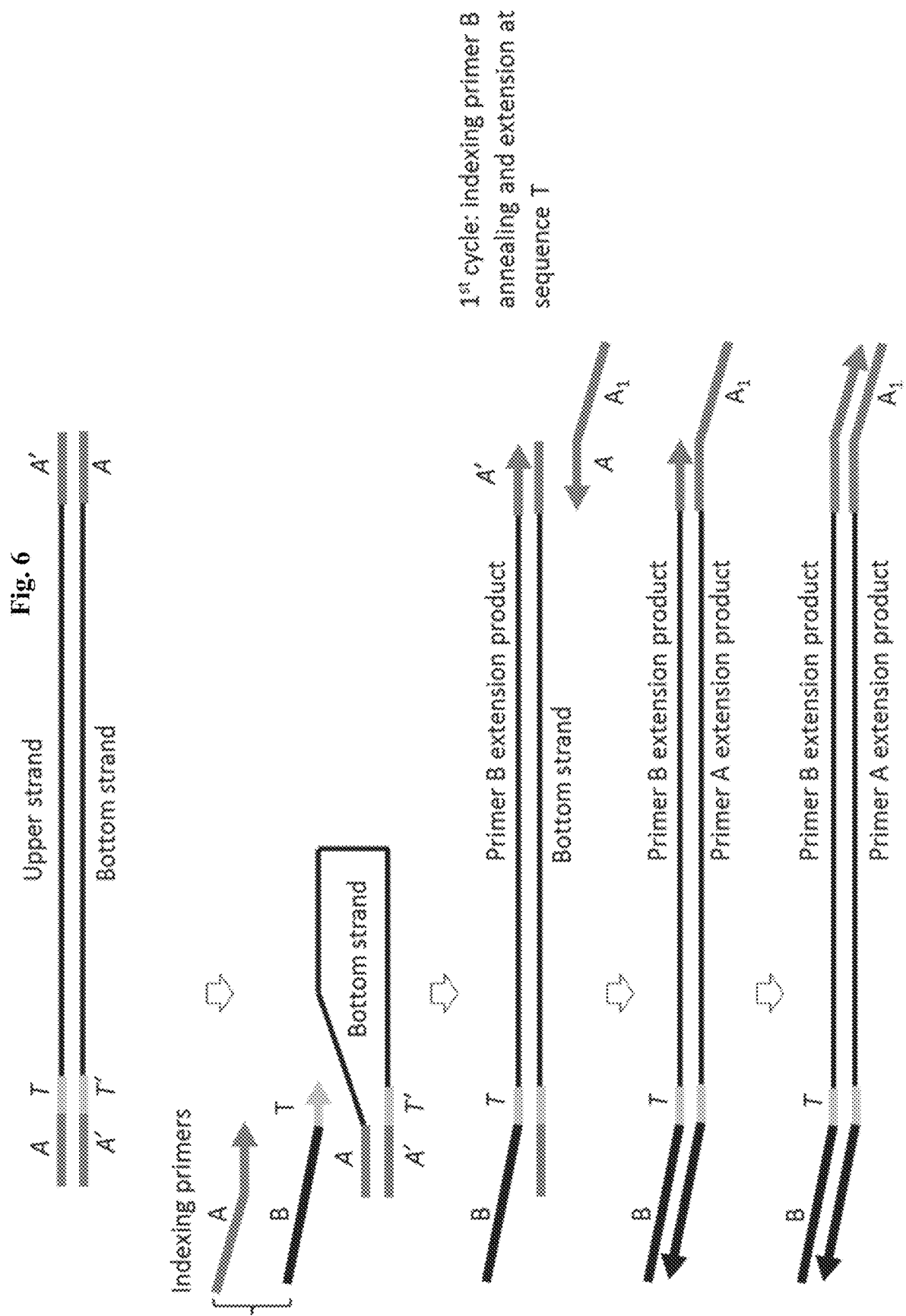
FIG. 6 depicts how the first indexing primer with NGS adapter B anneals to the first indexing primer sequence T in the denatured amplicon to extend and complete the B adapter sequence for NGS library construction, followed by annealing of the second indexing primer $(A+A_1)$ to the universal sequence A to extend and complete the second adapter sequence in the second PCR cycle.

In the final step of this novel amplicon workflow, an indexing PCR step completes the NGS adapter sequences and additionally incorporates sample specific index sequences to enable multiplexed sequencing (see FIGS. 4-6). It is during this PCR amplification step that the asymmetric, internally located first indexing primer sequence T plays an important role. Amplification by indexing primer pairs is initiated by a first priming event of the first indexing primer that includes at least a portion of the first indexing primer sequence T, where the primer additionally comprises a 5' tail including the NGS adapter sequence B and a sample specific index sequence. This priming event readily occurs because the first indexing primer sequence T has no self-complementary sequence that would generate stable secondary structure at the annealing temperature that would interfere or compete with primer annealing (see FIG. 6). Because the first indexing primer corresponding to the NGS adapter B primes internally to the universal sequence, the resulting primer extension product eliminates the distally located universal sequence A that was present on the template strand. Therefore, in the next PCR cycle, the second indexing primer that includes a portion or all of the universal sequence, which also additionally comprises a 5' tail including a sample specific index sequence and the NGS adapter $A_1$ (or the combination of at least a portion of A and $A_1$ if the universal sequence includes a portion of the NGS adapter), also readily primes to its complementary adapter sequence because the region of self-complementarity that would interfere or compete with primer annealing has been removed. Subsequent PCR cycles are continued until the desired product yield is achieved. A final purification step prior to library quantification and sequencing is then performed by methods known in the art.

Figure 3:
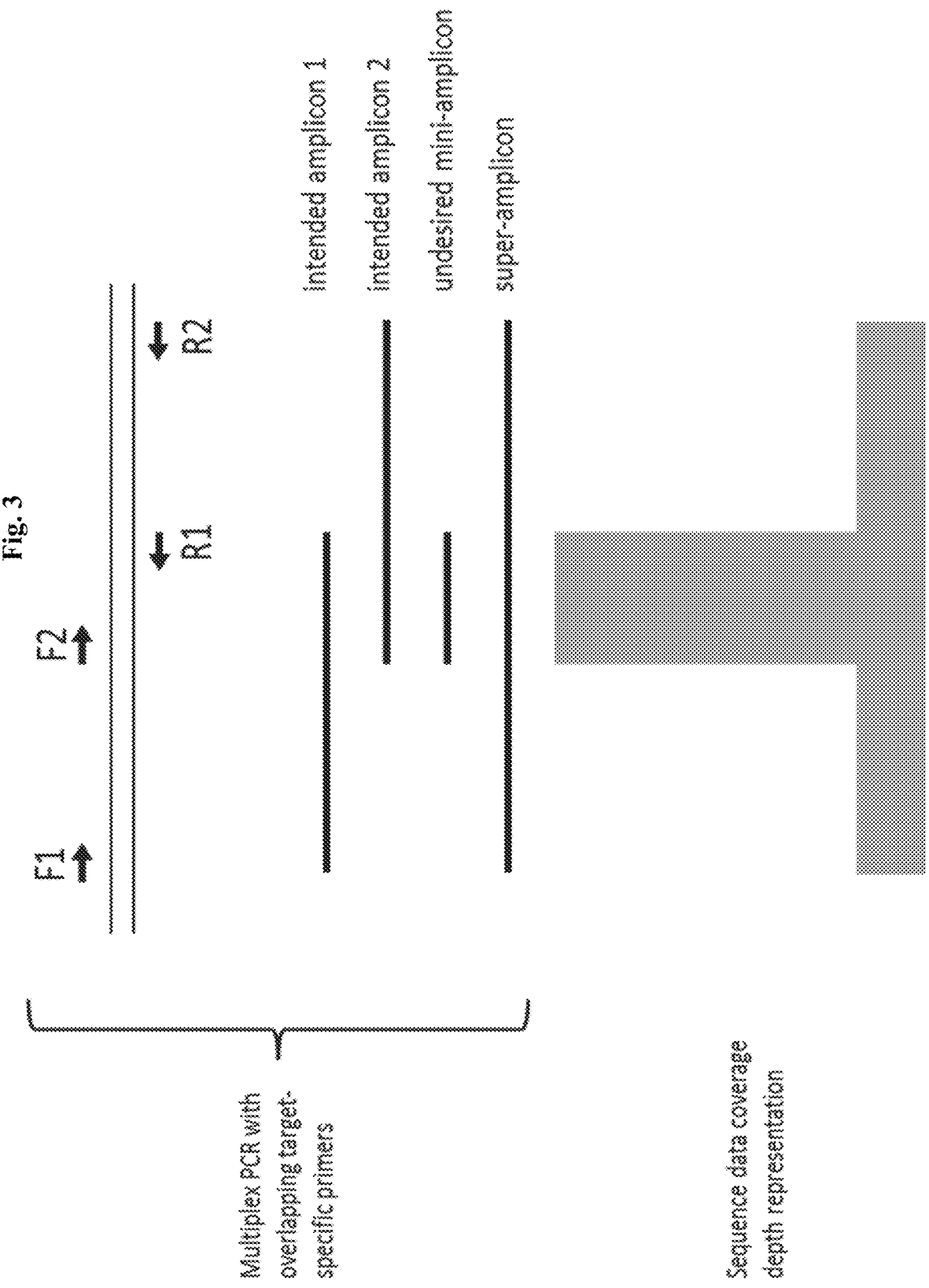
FIG. 3 depicts the products that can form from two overlapping primer pairs and the corresponding sequence data coverage depth, demonstrating that the undesired mini-amplicon can dominate the PCR and lead to a coverage imbalance in the sequencing data.

Additionally, as previously mentioned, methods for multiplexed PCR for targeted NGS libraries that are capable of amplifying overlapping targets for contiguous coverage in a single tube format is desired. The method disclosed herein is capable of achieving this effect (FIG. 3). In the case of two primer pairs that have overlapping target regions, 4 possible amplicons can be generated: an amplicon specific to each of the two primer pairs F1, R1 and F2, R2, a super-amplicon resulting from amplification of the two distal primers F1 and R2 and a mini-amplicon resulting from amplification of the two proximal primers F2, R1. To avoid having the mini-amplicon dominate the multiplexed PCR reaction (short amplicons such as this and primer dimers often dominate amplification reactions due to their short length and ease of amplification), most methods separate overlapping primer pairs into two tubes, which is effective but doubles the workload and required DNA input quantity.

In any of the foregoing embodiments, the purification step(s) can be performed by methods known in the art. In some embodiments, the purification step between each PCR cycle, or after the final PCR cycle, can include adding SPRI beads to the PCR mixture, separating the SPRI beads from the mixture and optionally, separating the amplicons from the SPRI beads. In some embodiments, the purification step can be performed by adding a single strand-specific exonuclease to the PCR reaction mixture and incubation the mixture under conditions sufficient for the single strand-specific exonuclease to digest single-stranded nucleic acid molecules, such as unused primers, and heating the mixture under conditions sufficient to inactivate the single strand-specific exonuclease. In some embodiments, the single strand-specific exonuclease is Exonuclease I.

Before subsequent PCR steps are performed, a PCR reagent mixture can be added to the mixture or sample sufficient for the subsequent PCR step can be performed. In some embodiments, additional DNA polymerase and deoxynucleoside triphosphates (dNTPs) may not be required if there are some remaining in the mixture. To the extent that additional DNA polymerase is added, it can be the same as or different from the DNA polymerase used in the preceding PCR step(s). In some embodiments, the PCR reagent mixture can include dNTPs and a DNA polymerase.

The methods disclosed herein enable overlapping amplicons to be created in a single tube, because due to the presence of the universal sequence at each terminus, the short mini-amplicons will be subject to stable secondary structure at the annealing temperature which results in less efficient amplification by the single universal primer. In contrast, the larger intended and super amplicons have a less stable self-complementary secondary structure at the annealing temperature and can be readily primed by the universal primer. Therefore, even if the mini-amplicons are produced during the initial target-specific PCR cycles, they will not be efficiently amplified due to the stable self-complementarity of the universal sequence A at the termini of each denatured amplicon at the annealing temperature. As a result, using methods disclosed herein, only the amplicons specific to each primer pair and the super-amplicon are produced from high quality, high molecular weight DNA input. When truncated Illumina P5 adapter sequence include in the target-specific forward primer.

Table 1 below provides exemplary target-specific primers, universal primers and indexing primer designs which can be used with the Illumina NGS platform.

Table 1

| # | Target-specific primers | Universal primer | Indexing primers | Tm |
|---|---|---|---|---|
| 1 | Reverse: 5'-TCAGACGTGTGCTCTTCCGATCT-ggg...ggg-3'<br>Forward: 5'-TCAGACGTGTGCTCTTCCGATCT<br>ACGACGCTCTTCCGATCT-ggg...ggg-3' | P7tr:<br>5'-TCAGACGTGT<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3 | 63.6<br><br>67.7 |
| 2 | Reverse: 5'-TCAGACGTGTGCTCTTCCGATCT-gggggggggggggggggg-3'<br>Forward: 5'-TCAGACGTGTGCTCTTCCGATCT<br>CGACGCTCTTCCGATCT-ggg...ggg-3' | P7tr:<br>5'-TCAGACGTGT<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3 | 61.5<br><br>67.7 |
| 3 | Reverse: 5'-TCAGACGTGTGCTCTTCCGATCT-gggggggggggggggggg-3'<br>Forward: 5'-TCAGACGTGTGCTCTTCCGATCT<br>GACGCTCTTCCGATCT-ggg...ggg-3' | P7tr:<br>5'-TCAGACGTGT<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3 | 58.4<br><br>67.7 |
| 4 | Reverse: 5'-CCTACACGACGCTCTTCCGATCT-gggggggggggggggggg-3'<br>Forward: 5'-CCTACACGACGCTCTTCCGATCT<br>ACGTGTGCTCTTCCGATCT-ggg...ggg-3' | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3 | 67.7<br><br>64 |
| 5 | Reverse: 5'-CCTACACGACGCTCTTCCGATCT-gggggggggggggggggg-3'<br>Forward: 5'-CCTACACGACGCTCTTCCGATCT<br>CGTGTGCTCTTCCGATCT-ggg...ggg-3' | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3' | 67.7<br><br>62.1 |
| 6 | Reverse: 5'-CCTACACGACGCTCTTCCGATCT-gggggggggggggggggg-3'<br>Forward: 5'-CCTACACGACGCTCTTCCGATCT<br>GTGTGCTCTTCCGATCT-ggg...ggg-3' | P5tr:<br>5'-CCTACACGACG<br>CTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCT-3' | 67.7<br><br>59.2 |
| 7 | Reverse: 5'-CCTACACGACGCTCTTCCGATCT-gggggggggggggggggg-3<br>Forward: 5'-CCTACACGACGCTCTTCCGATCT<br>GCGCGCGG-ggg...ggg-3 | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCTGCGCGC<br>GG-3 | 67.7<br><br>49.1 |
| 8 | Reverse: 5'-CCTACACGACGCTCTTCCGATCT-gggggggggggggggggg-3'<br>Forward: 5'-CCTACACGACGCTCTTCCGATCT<br>GCTCTTCCGATCTGCGC-ggg...ggg-3' | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCTGCGC-3' | 67.7<br><br>63.3 |
| 9 | Reverse: 5'-CCTACACGACGCTCTTCCGATCT-gggggggggggggggggg-3'<br>Forward: 5'-CCTACACGACGCTCTTCCGATCT<br>GCTCTTCCGATCTGCG-ggg...ggg-3' | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCTGCG-3' | 67.7<br><br>60 |
| 10 | Reverse: 5'-CCTACACGACGCTCTTCCGATCT-gggggggggggggggggg-3'<br>Forward: 5'-CCTACACGACGCTCTTCCGATCT<br>GCTCTTCCGATCTGC-ggg...ggg-3' | P5tr:<br>5'-CCTACACGAC<br>GCTCTTCCGATCT-3' | i5: 5'-AATGATACGGCGACCACCGAGATCTACAC[i5]<br>ACACTCTTTCCCTACACGACGCTCTTCCGATCT-3'<br>I7: 5' CAAGCAGAAGACGGCATACGAGAT[i7]<br>GTGACTGGAGTTCAGACGTGTGCTCTTCCGATCTGC-3' | 67.7<br><br>56.7 | cross-linked FFPE DNA or fragmented DNA (particularly circulating cell-free DNA that is in the 165 bp range) is used, formation of the super-amplicon is reduced since template length or integrity cannot support an amplicon of this size, and only the amplicons specific to each primer pair are produced.

Figure 7:
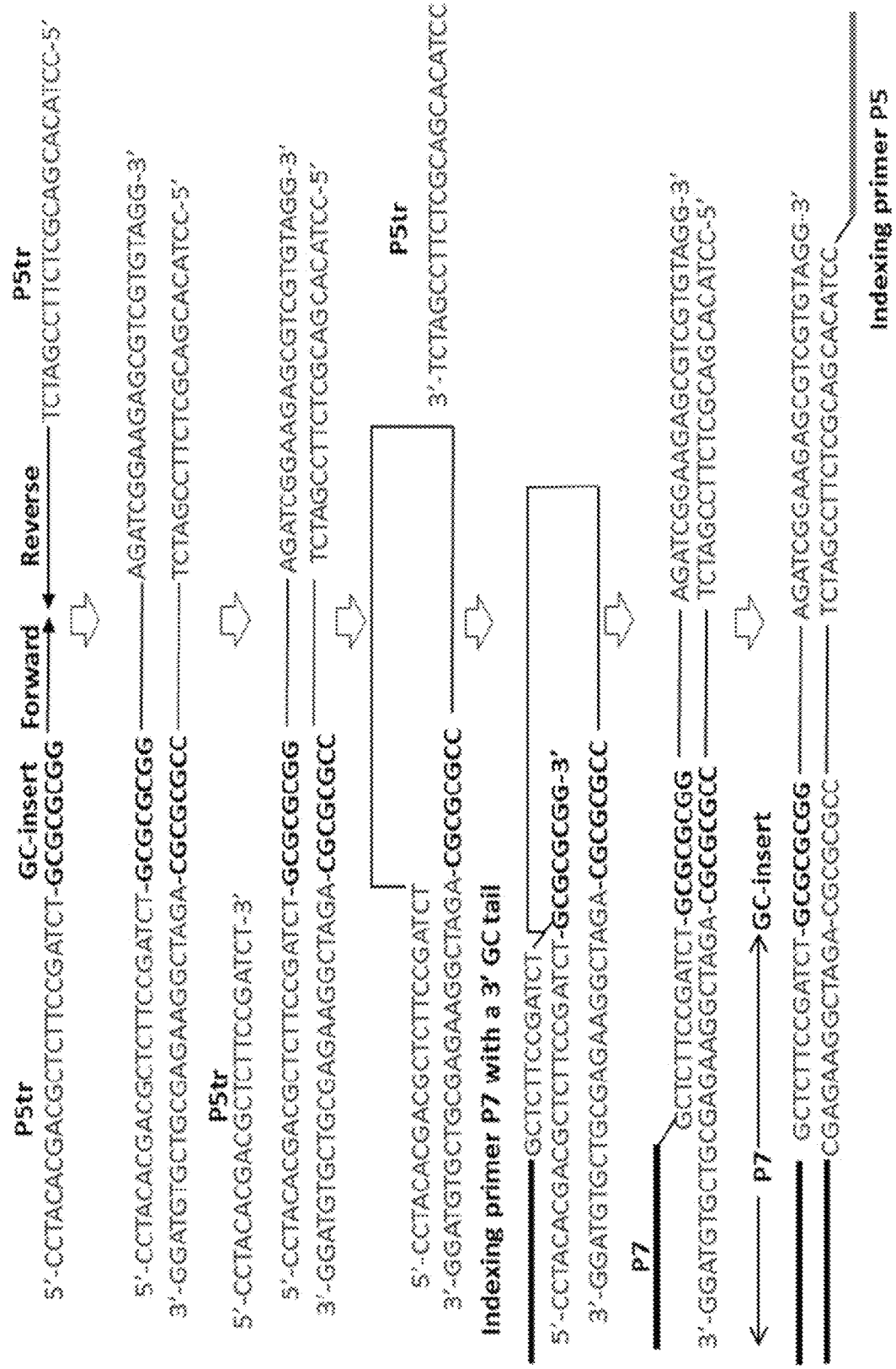
FIG. 7 depicts a specific embodiment where the universal sequence A is a portion of the P5 Illumina adapter, and the first indexing primer sequence T is a synthetic sequence comprising GC-rich content. This allows the Illumina P7 adapter to be introduced by a P7 indexing primer that has a 3' sequence that corresponds to the GC-rich first indexing primer sequence T, followed by annealing and extension of the P5 indexing primer on the P5 universal sequence.
Figure 8:
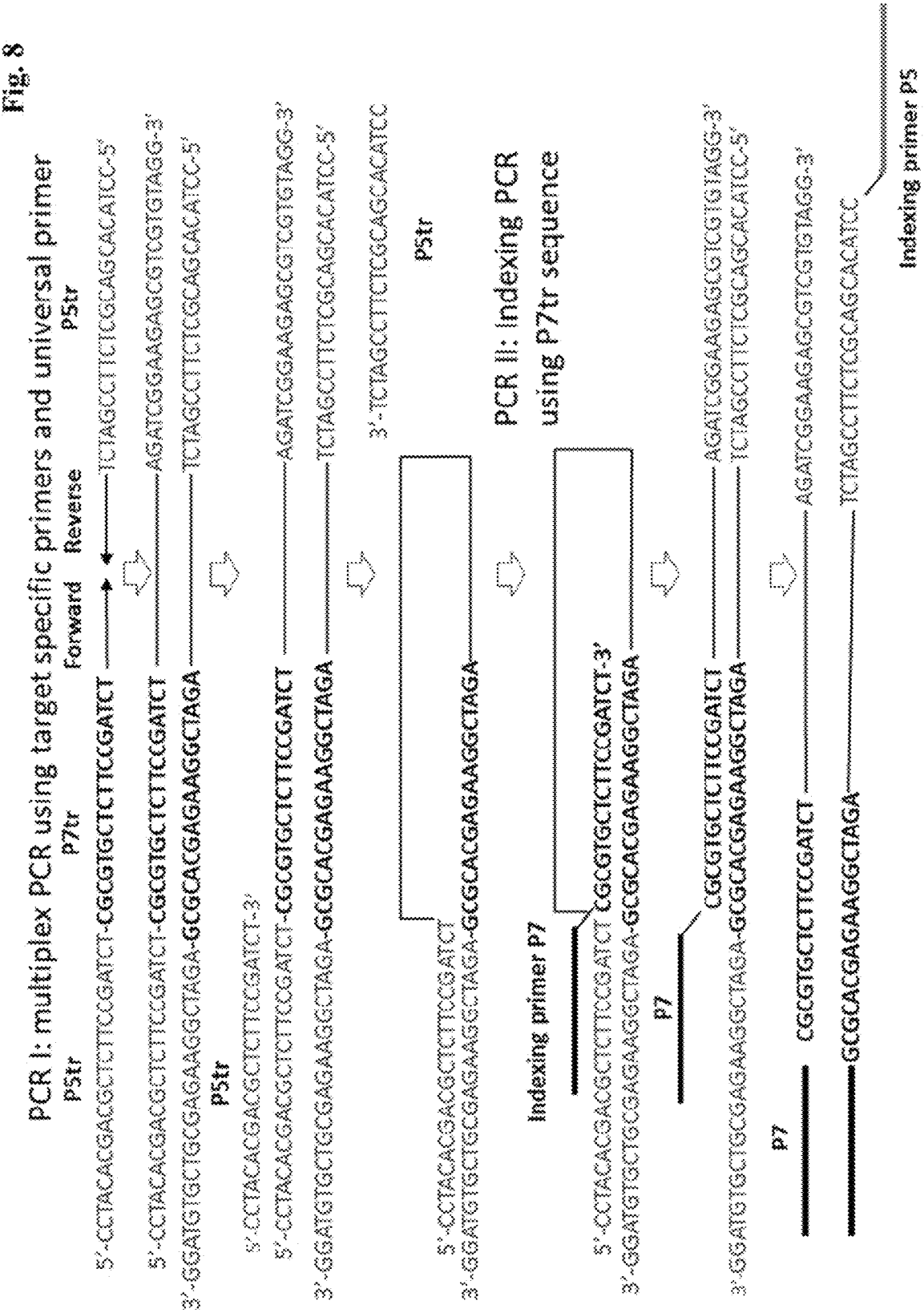
FIG. 8 depicts a specific embodiment where the universal sequence A is a portion of the P5 Illumina adapter, and the first indexing primer sequence T is a portion of the Illumina P7 adapter. This allows the remainder of the Illumina P7 adapter to be introduced by a P7 indexing primer in the first indexing PCR cycle, followed by annealing and extension of the P5 indexing primer on the P5 universal sequence in the second cycle.

FIGS. 7-9 depict embodiments of the methods of the present disclosure. FIG. 7 depicts a workflow where the target-specific forward primer includes a GC-rich sequence where indexing is completed with an Illumina P7 adapter and a P5 adapter. FIG. 8 depicts a workflow where indexing is completed on a truncated Illumina P7 adapter sequence included in the target-specific forward primer. FIG. 9 depicts a similar workflow where indexing is completed on a Table 1 depicts example primer sequences for different embodiments using Illumina adapter sequences, where the target specific primers (SEQ ID NOS 201-204, 203, 205-207, 206, 208, 206, 209, 206, 210, 206, 211, 206, 212, 206 and 213, respectively, in order of appearance), the universal primer (SEQ ID NOS 199, 199, 199, 191, 191, 191, 191, 191, 191 and 191, respectively, in order of appearance), and the corresponding indexing primer sequences (SEQ ID NOS 214-217, 214-217, 214-217, 214-217, 214-217, 214-217, 214-216, 218, 214-216, 219, 214-216, 220, 214-216 and 221, respectively, in order of appearance) are shown, with annealing Tm of the indexing primers. In Table 1 above, underlined sequences represent the sequence of the T insert (first indexing primer sequence), g indicates genomic portions of the target-specific primers and $T_m$ represents the melting temperature of the indexing primers during the first 2 PCR cycles when they prime a truncated amplicon library. Once the indexing sequence become integrated into the amplicon sequence their $T_m$ increases.

Table 2 below provides exemplary target-specific primers, universal primer, and indexing (barcoding primers) for the Ion NGS platform.

TABLE 2

| # | Target-specific primers | Universal Primer |
|---|---|---|
| 1 | 5'-CCTCTCTATGGGCAGTCGGTGAT-ggg...ggg-3'<br>5'-CCTCTCTATGGGCAGTCGGTGAT<br>CGATGCGCGCGG-ggg...ggg-3' | 5'-<br>CCTCTCTATGGGCAGTCGGTGAT-3' |
| | Indexing (barcoding) primers | $T_m$ (° C.) |
| | P1: 5'-CCACTACGCCTCCGCTTTCCTCTCT<br>ATGGGCAGTCGGTGAT-3' | 67.6 |
| | A: 5'-<br>CCATCTCATCCCTGCGTGTCTCCGACTCA<br>G[Barcode]CGATGCGCGCGG-3' | 60.8 |

Table 2 depicts example primer sequences for different embodiments using Ion Torrent adapter sequences, where the target specific primers (SEQ ID NOS 222-223, respectively, in order of appearance), the universal primer (SEQ ID NO: 224), and the corresponding indexing primer sequences (SEQ ID NOS 225-227, respectively, in order of appearance) are shown, with annealing $T_m$ of the indexing primers. In Table 2 above, underlined sequences represent the sequence of the T insert (first indexing primer sequence), g indicates genomic portions of the target-specific primers and $T_m$ represents the melting temperature of the indexing primers during the first 2 PCR cycles when they prime a truncated amplicon library. Once the indexing sequence become integrated into the amplicon sequence their $T_m$ increases.

Primer Concentration

Individual target-specific primers using the 2 step PCR method can by way of example but not limitation have a concentration of 1 nM to 100 nM or more where the preferred range is 1 nM-20 nM. Individual target-specific primers using the 3 step PCR method that optionally uses MIDs can by way of example but not limitation have a concentration of 50 nM to 500 nM or more where the preferred range is 100 nM-400 nM. For both workflows, the individual primer concentrations are within the range but not necessarily all at the same molarity, as primer pairs with higher efficiency are used at a lower primer concentration than primer pairs with a lower efficiency. By balancing the molarity of each primer pair, more even target amplification can be achieved so that sequence coverage is more uniform in order to reduce sequencing cost. The universal primer for both the 2 step (added with target-specific primers in the first PCR) and 3 step (added alone in the second PCR) workflows can, by way of example but not limitation, be used at a concentration from 1 uM-10 uM or more, where the preferred range is a concentration of 5-10 uM. During the final step of PCR, the concentration of individual indexing primers for both the 2 step and 3 step PCR can be 100 nM to 1 uM or more where the preferred concentration range is 300-600 nM.

Polymerases and Other Enzymes

The disclosed methods can utilize various DNA polymerases which can be used in the multiplexed, universal and indexing PCR reactions. The error rate during amplification can be improved when using high fidelity Pfu DNA polymerase, Phusion DNA polymerase, KAPA HiFi DNA polymerase (Roche), Q5 DNA polymerase (New England Biolabs), and PrimeSTAR GXL Polymerase (Clontech Takara) or their derivatives and analogs. Additionally, given that the universal primer used in the second phase of the amplification reaction comprises unmodified bases, it is not necessary to utilize high fidelity DNA polymerases that are tolerant of modified bases, such as KAPA HiFi U+ polymerase, Themo Phusion U and Enzymatics VeraSeq Ultra, each of which has reduced fidelity as a result of the tolerance of modified bases. Given the use of high fidelity enzymes that possess 3' to 5' exonuclease activity in the amplification reaction, both target-specific asymmetric primers and the universal primer optionally comprise nuclease-resistant modifications at their 3' termini; these include phosphorothioate linkages, 2'-O-Methyl or methylphosphonate modifications. Similarly, in some embodiments, the first indexing primer and second indexing primer can include these modifications. These enable more specific and efficient priming when using a proofreading polymerase that possesses 3' to 5' exonuclease activity.

Alternatively, Taq Polymerase and its derivatives, available from a variety of commercial sources, can be used for amplification. Since Taq Polymerase has excellent mismatch discrimination during priming events, it can improve the specificity of target amplification, and the spiking-in of a proof-reading polymerase can help improve fidelity of amplification. For the polymerases disclosed, use of antibody or aptamer based hot start additives can also increase the specificity of priming and reduce primer dimer formation. In the absence of hot start additives, reactions must be set up on ice and then placed into a pre-heated thermocycler to achieve the denaturing temperature as rapidly as possible.

As mentioned previously, to remove unused oligonucleotides from each PCR reaction, a purification such as a SPRI-bead based cleanup step can be performed. These include Beckman Coulter Ampure XP and SPRIselect beads. Alternatively, Exonuclease I and other single strand-specific exonucleases can be used to digest unused oligonucleotides, since the polymerase and buffer conditions are the same for each PCR, there is no need for a buffer exchange. Following exonuclease digestion, a heat inactivation step can be performed prior to adding oligonucleotides for the next PCR step. Following the last PCR, it is necessary to perform a purification step to prepare the targeted amplicon library for sequencing.

Thermocycling Conditions

Three-step PCR method: For the first PCR using target-specific primers, 2-3 or more cycles of the following touchdown PCR cycling program can be used: 2-4 minutes at 62+/−8° C., 2-4 minutes at 60+/−8° C., 2-4 minutes at 58+/−8° C., and 1 or more minutes at 65+/−8° C. to generate target-specific amplicons containing molecular identifiers. Alternatively, 2 to 3 or more long annealing and extension cycles of 2 to 10 minutes each at 62+/−8° C. can be performed. A purification or exonuclease digestion is then performed to remove target-specific primers and prevent overwriting the original molecular identifier in subsequent amplification steps. A second reaction for amplification of target-specific amplicons with a universal primer where mini-amplicons and primer dimers are inefficiently amplified is run using 6 to 30 cycles at 10 seconds at 98° C., 15 seconds at 60+/8° C., and 1 minute at 66+/−8° C. for amplification of target-specific amplicons. Ideally the number of cycles is a minimum of 10 to 20 or more to produce a 1000× or greater selective amplification of the longer intended amplicons and super-amplicons relative to primer dimers and mini-amplicons. The reaction is then purified or primers removed by exonuclease treatment and a third reaction containing the NGS adapter indexing primers is performed using 2 to 12 cycles of 10 seconds at 98° C., 15 seconds at 60+/−8° C., and 1 minute at 66+/−8° C. to add sample indexes and full-length NGS adapters to the amplicons. For each PCR, hot start polymerase activation can be performed according to manufacturer's recommendations. By way of example, but not limitation, the cycle time can be 1, 2, 3, 4, 5, 6, 7, 8, 9, 10, 11, 12, 13, 14, 15, 16, 17, 18, 19, 20 or more minutes.

Two-step PCR method: For the first PCR using target-specific primers and the universal primer, 2 to 4 or more long annealing and extension cycles of 2 to 10 minutes each at 62+/−8° C. can be performed in order to generate target-specific amplicons from the low concentration target specific primers. Then the remaining cycles of this PCR are performed for selective amplification of target-specific amplicons over mini-amplicons and primer dimers using 6-30 cycles at 10 seconds at 98° C., 15 seconds at 60+/8° C., and 1 minute at 66+/−8° C. Ideally the number of cycles is a minimum of 10 to 20 or more to produce a 1000× or greater selective amplification of the longer intended amplicons and super-amplicons relative to primer dimers and mini-amplicons. The reaction is then purified or primers removed by exonuclease treatment and a second PCR reaction containing the NGS adapter indexing primers is performed using 2 to 12 cycles of 10 seconds at 98° C., 15 seconds at 60+/−8° C., and 1 minute at 66+/−8° C. to add sample indexes and full-length NGS adapters to the amplicons. For each PCR, hot start polymerase activation can be performed according to manufacturer's recommendations. By way of example, but not limitation, the cycle time can be 1, 2, 3, 4, 5, 6, 7, 8, 9, 10, 11, 12, 13, 14, 15, 16, 17, 18, 19, 20 or more minutes.

Selective amplification of target specific amplicons can be performed using an appropriate number of PCR cycles for the degree of amplification desired. By way of example but not limitation, 6 to 30 or more PCR cycles can be used to amplify target specific amplicons using the universal primer, for example, at least 6, 7, 8, 9 10, 11, 12, 13, 14, 15, 16, 17, 18, 19, 20, 21, 22, 23, 24, 25, 26, 27, 28, 29 or 30 or more PCR cycles can be used. In some embodiments, by way of example but not limitation, 6-10, 10-20, 10-30 or 20-30 PCR cycles can be used for target specific amplicon amplification.

Indexing PCR can be performed using an appropriate number of PCR cycles for the degree of amplification desired. By way of example but not limitation, 2 to 12 or more PCR cycles can be used to complete indexing of the target specific amplicons, for example, at least 2, 3, 4, 5, 6, 7, 8, 9, 10, 11, 12 or more PCR cycles can be used. In some embodiments, by way of example but not limitation, 2-10 or 5-10 PCR cycles can be used for indexing PCR.

Input DNA

The quantity of target nucleic acid to be used for target amplification can be determined by the desired sensitivity of low frequency allele detection, as well as the purity and integrity of the DNA sample. For example, use of 10 ng enables a limit of detection of 0.5% when using MIDs, and 20 ng enables a limit of detection of 0.25% when using MIDs, where it is possible to enable a limit of detection as low as 0.1% with higher input quantities up to 50 ng. Higher input quantities are required for the lower limit of detection in order to guarantee that the low frequency allele is present in the reaction for detection. It is recommended that a minimum of 10 copies of the allele of interest is placed into the reaction in order to ensure that sufficient low copy number will be present for detection. For example, if one wished to determine a 1% allele frequency from 1 ng human DNA, this would represent 3/330 copies of the genome, and the likelihood few copies are present due to Poisson distribution of DNA fragments is low. Alternatively, if one wished to determine a 1% allele frequency from 10 ng human DNA, this would represent 33/3,300 copies of the genome, and the likelihood sufficient copies are present in the reaction is high. For this reason, it is important to carefully quantify the input DNA so that the desired sensitivity results. For high molecular weight, high quality DNA, using a fluorometric method such as Qubit or PicoGreen properly estimates the quantity of usable DNA for an assay. For damaged DNA such as FFPE that has cross-links and other damage, using a qPCR assay to determine amplifiable content such as human ALU repeat primers can be used. Similarly, for cfDNA, it is important to know the cell-free vs. cellular DNA fraction as only the cell free fraction will carry the allele of interest, so a similar ALU repeat assay can be used to calculate both amplifiable content as well as the ratio of cell-free to cellular DNA, if different sized ALU assays are used.

Kits

The present disclosure also provides kits for performing the methods disclosed herein. The kits can include any of the components necessary to perform the steps of the disclosed methods. In some embodiments, a next generation sequencing (NGS) kit is provided that includes a first target-specific primer pair, a second target-specific primer pair, a universal primer that includes at least a portion of a universal sequence, a first indexing primer that includes a first indexing primer sequence and a first adaptor sequence, a second indexing primer that includes at least a portion of the universal sequence and a second adaptor sequence that is different from the first adaptor sequence, where the first target-specific primer pair includes a first target-specific primer that includes a first target-specific sequence that is complementary to a first target sequence on a substrate nucleic acid molecule, the first indexing primer sequence and the universal sequence and a second target-specific primer that includes a second target-specific sequence that is complementary to a second target sequence on the substrate nucleic acid molecule and the universal sequence, and where the second target-specific primer pair includes a third target-specific primer that includes a third target-specific sequence that is complementary to a third target sequence on the substrate nucleic acid molecule, the first indexing primer sequence and the universal sequence, and a fourth target-specific primer that includes a fourth target-specific sequence that is complementary to a fourth target sequence on the substrate nucleic acid molecule and the universal sequence. In some embodiments, the kit can further include a first DNA polymerase. In some embodiments, the kit can further include both a first DNA polymerase and deoxynucleoside triphosphates (dNTPs). In some embodiments, the kit can further include a second DNA polymerase. In some embodiments, the kit can further include third DNA polymerase. It should be understood that the target-specific primer pairs, universal primer and indexing primers can have the features herein disclosed in foregoing embodiments and that these features can, to the extent they are not inconsistent, be combined. In some embodiments, the kit can further include SPRI beads. In some embodiments, the kit can further include 20% PEG-8000/2.5M NaCl solution. In some embodiments, the kit can include single strand-specific exonuclease. By way of example, but not limitation, the single strand-specific exonuclease can be Exonuclease I.

It should be understood that the following examples are intended to illustrate the methods of the present disclosure and are not intended to limit the scope of the disclosure.

EXAMPLES

Example 1

Rationale: A 21 amplicon panel was designed to cover the coding regions of the TP53 gene where the forward target specific primer included a truncated Illumina adapter P5 sequence as the first indexing primer sequence and a truncated Illumina adapter P7 sequence as the universal sequence. Designs included significant overlap between amplicons to demonstrate the absence of mini-amplicon dominating the reaction.

Materials:
  Human genomic DNA (Coriell Institute, NA12878)
  Q5® Hot Start High-Fidelity 2× Master Mix (NEB, cat #M0494)
  42 target-specific primers (Table 4)
  Universal primer containing truncated P7 adapter sequence 16-365 (Table 3)
  Indexing primer consisting of full-length P7 adapter sequence 17-1197 (Table 3)
  Indexing primer consisting of full-length P5 adapter sequence 17-946 (Table 3)
  SPRIselect reagent (Beckman Coulter, B23318)
  20% PEG-8000/2.5M NaCl solution
  DNA Suspension Buffer, 10 mM Tris, 0.1 mM EDTA, pH 8.0 (Teknova, cat #T0227)
  Qubit dsDNA HS Assay Kit (ThermoFisher Scientific, cat #Q32851)

Method: Human genomic DNA was diluted in DNA suspension buffer. A first reaction for target selection and molecular identifier incorporation was performed in 30 µl. For each amplicon the forward target-specific primer contained a truncated Illumina P5 adapter sequence as the first indexing primer sequence and the reverse target-specific primer contained a 10 base random N sequence that served as a molecular identifier. Both the forward and reverse target-specific primers also contained the same universal sequence at the 5' end that is a truncated Illumina P7 adapter sequence. This reaction consisted of 1×Q5 Hot Start High-Fidelity Master Mix, a mix of 42 target-specific primers present at different concentrations (Table 4) and averaging at 206 nM each, and 10 ng genomic DNA. The following cycling program was run on this reaction mix: 30 seconds at 98° C. followed by 2 cycles of 30 seconds at 98° C., 2 minutes at 62° C., 4 minutes at 60° C., 2 minutes at 58° C., and 1 minute at 65° C. to generate target-specific amplicons containing molecular identifiers and completed with 1 minute at 65° C. Two consecutive purifications were performed to maximize removal of target-specific primers and prevent overwriting the original molecular identifier in subsequent amplification steps. The first purification was done with 36 µl of SPRIselect beads (1.2× ratio) and the reaction was eluted in 30 µl TE but not removed from beads. A second purification was performed with 31.5 µl 20% PEG-8000/2.5M NaCl solution (1.05× ratio), eluted in 20 µl DNA Suspension Buffer, and transferred to a new tube. A second reaction for amplification of target-specific amplicons with a universal primer where mini-amplicons and primer dimers are inefficiently amplified was set up in 50 µl. This reaction contained 20 µl eluted reaction mix, 1×Q5 Hot Start High-Fidelity Master Mix, and 10 µM of the universal primer. The following cycling program was run on this reaction mix: 45 seconds at 98° C. followed by 22 cycles of 10 seconds at 98° C., 15 seconds at 60° C., and 1 minute at 66° C. for amplification of target-specific amplicons. The reaction was purified with 60 µl of SPRIselect beads (1.2× ratio) and the beads were resuspended in 30 µl of a third reaction mix containing 1×Q5 Hot Start High-Fidelity Master Mix, 500 nM of the P7 indexing primer, and 500 nM of the P5 indexing primer. The following cycling program was run on this reaction mix: 45 seconds at 98° C. followed by 6 cycles of 10 seconds at 98° C., 15 seconds at 60° C., and 1 minute at 66° C. to add sample indexes and full-length NGS adapters to the amplicons. The reaction was purified with 51 µl of 20% PEG-8000/2.5M NaCl solution (0.85× ratio) and the DNA was eluted in 20 µl DNA Suspension Buffer. Library was quantified using the Qubit dsDNA HS Assay Kit and sequenced on a MiniSeq (Illumina) with paired end reads of 151 bases.

Figure 10:
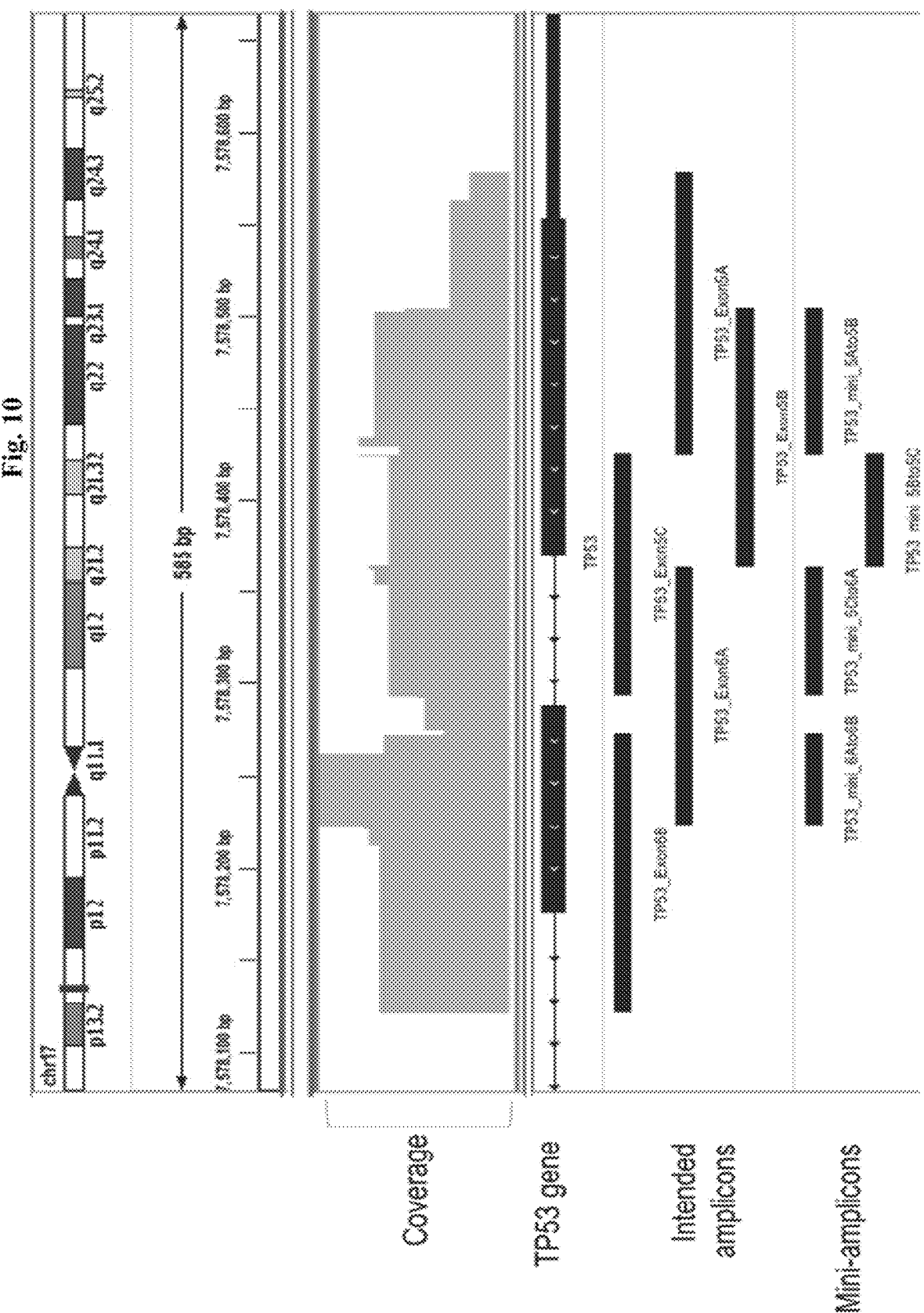
FIG. 10 depicts the coverage plot for the sequence data from Example 1. It is notable that coverage at the mini-amplicons is not significantly greater than the sum of the two overlapping intended amplicons.
Figure 11:
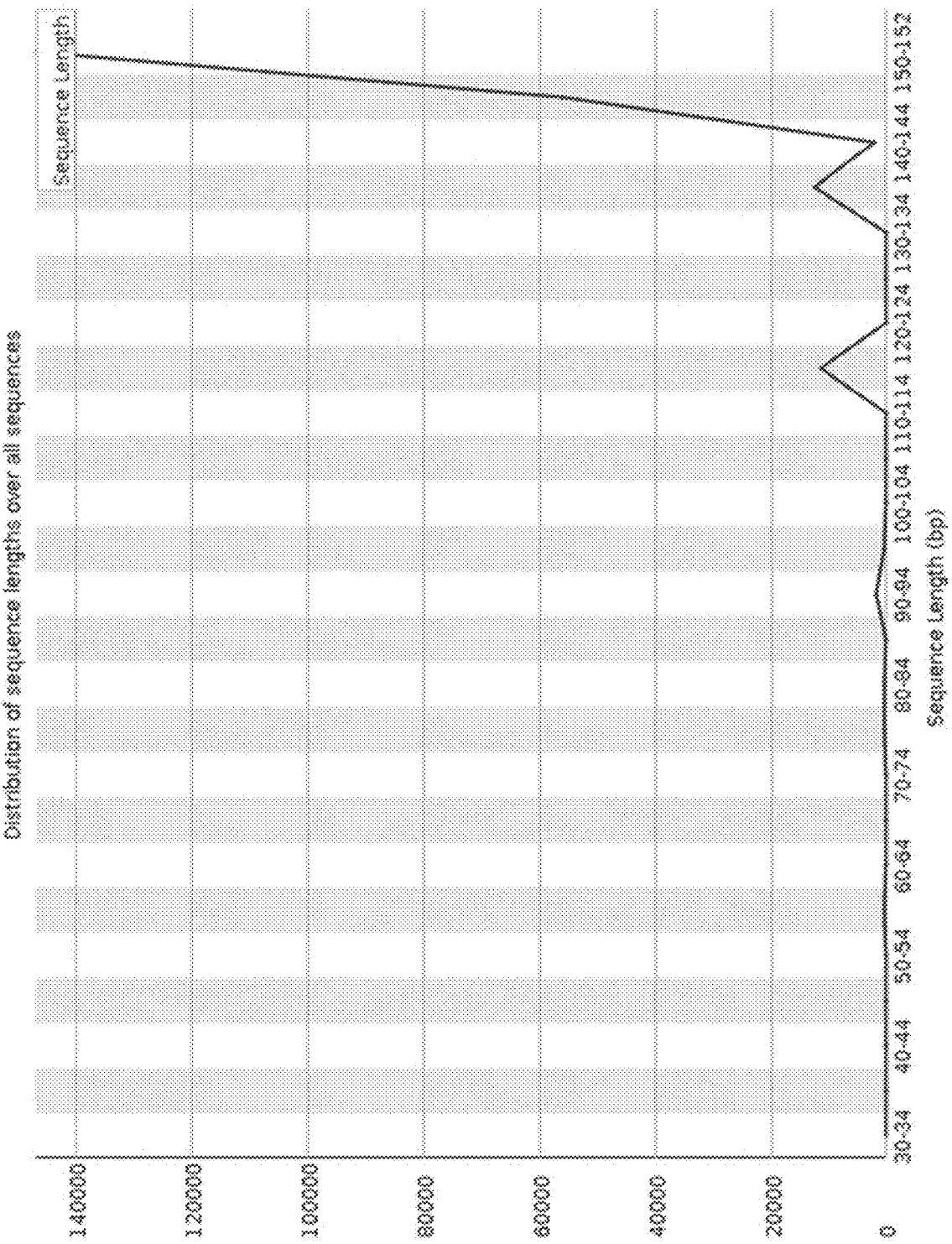
FIG. 11 depicts read lengths for the sequence data from Example 1. It is notable that there is not a significant number of short reads from primer dimers.

Results: The library quantification by Qubit was 9.1 nM. The 10 base unique molecular identifier was removed from the beginning of Read 2 for each read pair prior to aligning reads to the human genome and to the target region. The sequencing data was of high quality such that greater than 98% of reads aligned to the intended target regions. All 21 amplicons were represented in the final library and only one amplicon was covered at less than 20% of the mean amplicon coverage. FIG. 10 depicts the coverage prior to removal of PCR duplicates for 5 overlapping amplicons that cover TP53 exons 5 & 6. Mini-amplicons that can be produced by overlapping amplicons will dominate the reaction if they are not suppressed since short sequences are preferentially amplified and mini-amplicons can only be amplified to produce additional mini-amplicons while intended, full-length amplicons can be amplified to produce either mini-amplicons or full-length amplicons. FIG. 10 demonstrates that mini-amplicons never show more coverage than the sum of the overlapping amplicons and therefore production of mini-amplicons are not a major contributor to coverage. This indicates that mini-amplicons do not dominate the library as they are suppressed by formation of a stable secondary structure. Primer dimers are also minimal in the final library such that short reads with an insert size of less than 35 bases represent less than 0.1% of the total reads, the lower limit reported by Illumina software (FIG. 11).

Conclusions: A targeted asymmetric amplicon library was successfully made using a truncated Illumina P5 sequence introduced through one of the target specific primers. The sequencing demonstrated that mini-amplicons produced from overlapping amplicon design and primer dimers did not contribute significantly to the final library.

TABLE 3

Oligonucleotides used in Example 1

| Sequence Name | SEQ ID NO | Sequence (5'-3') |
|---|---|---|
| 16-365 | 1 | TCAGACGTGTGCTCTTCCGAT*C*T |
| 17-1197 | 2 | CAAGCAGAAGACGGCATACGAGATAGCTTCAGGTGACTGGAGTTCAGACGTGTGCTCTTCCGATCT |
| 17-946 | 3 | AATGATACGGCGACCACCGAGATCTACACATAGAGGCACACTCTTTCCCTACACGACGCTCTTCCGATCT |

*Phosphorothioated DNA bases (IDT)

TABLE 4

Target-Specific Oligonucleotides used in Example 1

| SEQ ID NO | Sequence (5'-3') | Final concentration in PCR (nM) |
|---|---|---|
| 4 | TCAGACGTGTGCTCTTCCGATCTCGACGCTCTTCCGATCTTAGCACTGCCCAACAACA*C*C | 154 |
| 5 | TCAGACGTGTGCTCTTCCGATCT(N1:25252525)(N1)(N1)(N1)(N1)(N1)(N1)(N1)(N1)AGACTTAGTACCTGAAGGGT*G*A | 154 |
| 6 | TCAGACGTGTGCTCTTCCGATCTCGACGCTCTTCCGATCTTGGGACGGAACAGCTTTG*A*G | 103 |
| 7 | TCAGACGTGTGCTCTTCCGATCT(N1:25252525)(N1)(N1)(N1)(N1)(N1)(N1)(N1)(N1)CCACCGCTTCTTGTCC*T*G | 103 |
| 8 | TCAGACGTGTGCTCTTCCGATCTCGACGCTCTTCCGATCTGGGTGCAGTTATGCCTC*A*G | 103 |
| 9 | TCAGACGTGTGCTCTTCCGATCT(N1:25252525)(N1)(N1)(N1)(N1)(N1)(N1)(N1)(N1)CGGCATTTTGAGTGTTAGACT*G*G | 103 |
| 10 | TCAGACGTGTGCTCTTCCGATCTCGACGCTCTTCCGATCTCTGACTGCTCTTTTCACCC*A*T | 103 |
| 11 | TCAGACGTGTGCTCTTCCGATCT(N1:25252525)(N1)(N1)(N1)(N1)(N1)(N1)(N1)(N1)GAGCAGCCTCTGGCATTC*T*G | 103 |
| 12 | TCAGACGTGTGCTCTTCCGATCTCGACGCTCTTCCGATCTTGAAGACCCAGGTCCAGAT*G*A | 154 |
| 13 | TCAGACGTGTGCTCTTCCGATCT(N1:25252525)(N1)(N1)(N1)(N1)(N1)(N1)(N1)(N1)GCTGCCCTGGTAGGTTTTC*T*G | 154 |
| 14 | TCAGACGTGTGCTCTTCCGATCTCGACGCTCTTCCGATCTGCATCTTATCCGAGTGGAA*G*G | 103 |
| 15 | TCAGACGTGTGCTCTTCCGATCT(N1:25252525)(N1)(N1)(N1)(N1)(N1)(N1)(N1)(N1)CACTGACAACCACCCTTAA*C*C | 103 |
| 16 | TCAGACGTGTGCTCTTCCGATCTCGACGCTCTTCCGATCTCATGTGTAACAGTTCCTGCA*T*G | 103 |
| 17 | TCAGACGTGTGCTCTTCCGATCT(N1:25252525)(N1)(N1)(N1)(N1)(N1)(N1)(N1)(N1)GGTCAGAGGCAAGCAG*A*G | 103 |
| 18 | TCAGACGTGTGCTCTTCCGATCTCGACGCTCTTCCGATCTCAGGTAGGACCTGATTTCCTT*A*C | 154 |
| 19 | TCAGACGTGTGCTCTTCCGATCT(N1:25252525)(N1)(N1)(N1)(N1)(N1)N(1)(N1)(N0TTCTTGCGGAGATTCTCTT*C*C | 154 |
| 20 | TCAGACGTGTGCTCTTCCGATCTCGACGCTCTTCCGATCTATGGTTCTATGACTTTGCCT*G*A | 128 |
| 21 | TCAGACGTGTGCTCTTCCGATCT(N1:25252525)(N1)(N1)(N1)(N1)(N1)(N1)(N1)(N1)AGCAGGCTAGGCTAAGCTA*T*G | 128 |
| 22 | TCAGACGTGTGCTCTTCCGATCTCGACGCTCTTCCGATCTCTGTGCAGCTGTGGGTT*G*A | 128 |

TABLE 4-continued

Target-Specific Oligonucleotides used in Example 1

| SEQ ID NO | Sequence (5'-3') | Final concentration in PCR (nM) |
|---|---|---|
| 23 | TCAGACGTGTGCTCTTCCGATCT(N1:25252525)(N1)(N1)(N1)(N1)(N1)(N1)(N1)(N1)(N1)GCTCACCATCGCTATCTG*A*G | 128 |
| 24 | TCAGACGTGTGCTCTTCCGATCTCGACGCTCTTCCGATCTAGCTGGGGCTGGAGA*G*A | 154 |
| 25 | TCAGACGTGTGCTCTTCCGATCT(N1:25252525)(N1)(N1)(N1)(N1)(N1)(N1)(N1)(N1)GTCATCCAAATACTCCACACG*C*A | 154 |
| 26 | TCAGACGTGTGCTCTTCCGATCTCGACGCTCTTCCGATCTCTCTGTCTCCTTCCTCTTCCT*A*C | 205 |
| 27 | TCAGACGTGTGCTCTTCCGATCT(N1:25252525)(N1)(N1)(N1)(N1)(N1)(N1)(N1)(N1)GTGCTGTGACTGCTTGTA*G*A | 205 |
| 28 | TCAGACGTGTGCTCTTCCGATCTCGACGCTCTTCCGATCTCGCACTGGCCTCATCT*T*G | 128 |
| 29 | TCAGACGTGTGCTCTTCCGATCT(N1:25252525)(N1)(N1)(N1)(N1)(N1)(N1)(N1)(N1)CTTCCAGTGTGATGATGGTG*A*G | 128 |
| 30 | TCAGACGTGTGCTCTTCCGATCTCGACGCTCTTCCGATCTCATGACGGAGGTTGTGA*G*G | 128 |
| 31 | TCAGACGTGTGCTCTTCCGATCT(N1:25252525)(N1)(N1)(N1)(N1)(N1)(N1)(N1)(N1)AGCAATCAGTGAGGAATCAG*A*G | 128 |
| 32 | TCAGACGTGTGCTCTTCCGATCTCGACGCTCTTCCGATCTCCTGGTTGTAGCTAACTAACT*T*C | 154 |
| 33 | TCAGACGTGTGCTCTTCCGATCT(N1:25252525)(N1)(N1)(N1)(N1)(N1)(N1)(N1)(N1)ACCATCGTAAGTCAAGTAGCA*T*C | 154 |
| 34 | TCAGACGTGTGCTCTTCCGATCTCGACGCTCTTCCGATCTTCCTCCCTGCTTCTGTC*T*C | 154 |
| 35 | TCAGACGTGTGCTCTTCCGATCT(N1:25252525)(N1)(N1)(N1)(N1)(N1)(N1)(N1)(N0CTGTCAGTGGGGAACAAGA*A*G | 154 |
| 36 | TCAGACGTGTGCTCTTCCGATCTCGACGCTCTTCCGATCTGCTGAATGAGGCCTTGGA*A*C | 179 |
| 37 | TCAGACGTGTGCTCTTCCGATCT(N1:25252525)(N1)(N1)(N1)(N1)(N1)(N1)(N1)(N1)CTTTCCAACCTAGGAAGGC*A*G | 179 |
| 38 | TCAGACGTGTGCTCTTCCGATCTCGACGCTCTTCCGATCTTCTTGCAGCAGCCAGA*C*T | 205 |
| 39 | TCAGACGTGTGCTCTTCCGATCT(N1:25252525)(N1)(N1)(N1)(N1)(N1)(N1)(N1)(N1)CCTGCCCTTCCAATGGA*T*C | 205 |
| 40 | TCAGACGTGTGCTCTTCCGATCTCGACGCTCTTCCGATCTTTACTTCTCCCCCTCCTC*T*G | 231 |
| 41 | TCAGACGTGTGCTCTTCCGATCT(N1:25252525)(N1)(N1)(N1)(N1)(N1)(N1)(N1)(N1)CTTCCCAGCCTGGGCA*T*C | 231 |
| 42 | TCAGACGTGTGCTCTTCCGATCTCGACGCTCTTCCGATCTCTGGCCCCTGTCATCTTC*T*G | 282 |
| 43 | TCAGACGTGTGCTCTTCCGATCT(N1:25252525)(N1)(N1)(N1)(N1)(N1)(N1)(N1)(N1)CAGGCATTGAAGTCTCATG*G*A | 282 |
| 44 | TCAGACGTGTGCTCTTCCGATCTCGACGCTCTTCCGATCTCCCCTAGCAGAGACCT*G*T | 1282 |
| 45 | TCAGACGTGTGCTCTTCCGATCT(N1:25252525)(N1)(N1)(N1)(N1)(N1)(N1)(N1)(N1)GCCCAACCCTTGTCCTT*A*C | 1282 |

*Phosphorothioated DNA bases (IDT)(N1:25252525)(N1)(N1)(N1)(N1)(N1)(N1)(N1)(N1): 10 hand-mixed random nucleotides (IDT)

Example 2

Rationale: A 20 amplicon panel was designed to cover an 891 base region of the BRCA2 gene, with additional coverage of the NRAS, PIK3CA, KIT, EGFR, BRAF, and KRAS genes, where the forward target specific primer included a synthetic GC-rich sequence as the first indexing primer sequence and a truncated Illumina P5 adapter as the universal sequence. Designs included significant overlap between amplicons to demonstrate the absence of mini-amplicons dominating the reaction.

Materials:
- Human genomic DNA (Horizon Diagnostics: HD701)
- Q5® Hot Start High-Fidelity 2× Master Mix (NEB, cat #M0494)
- 40 target-specific primers (Table 6)
- Universal primer 16-365 (Table 5)
- Indexing primer consisting of full-length P7 adapter sequence and a 3' terminal GC-rich sequence 17-754 (Table 5)
- Indexing primer consisting of full-length P5 adapter sequence 17-758 (Table 5)
- SPRIselect reagent (Beckman Coulter, B23318)
- 20% PEG-8000/2.5M NaCl solution
- DNA Suspension Buffer, 10 mM Tris, 0.1 mM EDTA, pH 8.0 (Teknova, cat #T0227)
- Qubit dsDNA HS Assay Kit (ThermoFisher Scientific, cat #Q32851)

Method: Human genomic DNA was diluted in DNA suspension buffer. A first reaction for target selection and amplification was performed in 30 µl. For each amplicon the forward target-specific primer contained a 6 base GC-rich sequence (GCGCGG) as the first indexing primer sequence. Both the forward and reverse target-specific primers also contained a universal primer sequence at the 5' end that is a truncated Illumina P5 sequence. This reaction consisted of 1×Q5 Hot Start High-Fidelity Master Mix, a mix of 40 target-specific primers present at different concentrations (Table 6) and averaging at 173.5 nM each, a universal primer at 10 µM and 10 ng genomic DNA. The following cycling program was run on this reaction mix: 30 seconds at 98° C. followed by 4 cycles of 10 seconds at 98° C., 5 minutes at 63° C., and 1 minute at 65° C. This was then immediately followed by 20 cycles of 10 seconds at 98° C. and 1 minute at 64° C. and completed with 1 minute at 65° C. Purification was then done with 36 µl of SPRIselect beads (1.2× ratio) and the reaction was eluted in 20 µl TE but not removed from beads. A second PCR reaction for indexing of target-specific amplicons was performed. This reaction consisted of 1×Q5 Hot Start High-Fidelity Master Mix, 600 nM of the P7 indexing primer containing the 3' GC-rich sequence that corresponds to the first indexing primer sequence introduced in the first PCR, and 600 nM of the P5 indexing primer that anneals to the universal sequence. The following cycling program was run on this reaction mix: 45 seconds at 98° C. followed by 6 cycles of 10 seconds at 98° C., 15 seconds at 60° C., and 1 minute at 66° C. to add sample indexes and full-length adapters to the amplicons. The reaction was purified with 51 µl of 20% PEG-8000/2.5M NaCl solution (0.85× ratio) and the DNA was eluted in 20 µl DNA Suspension Buffer. The library was quantified using the Qubit dsDNA HS Assay Kit and sequenced on a MiniSeq (Illumina) with paired end reads of 151 bases.

Figure 12:
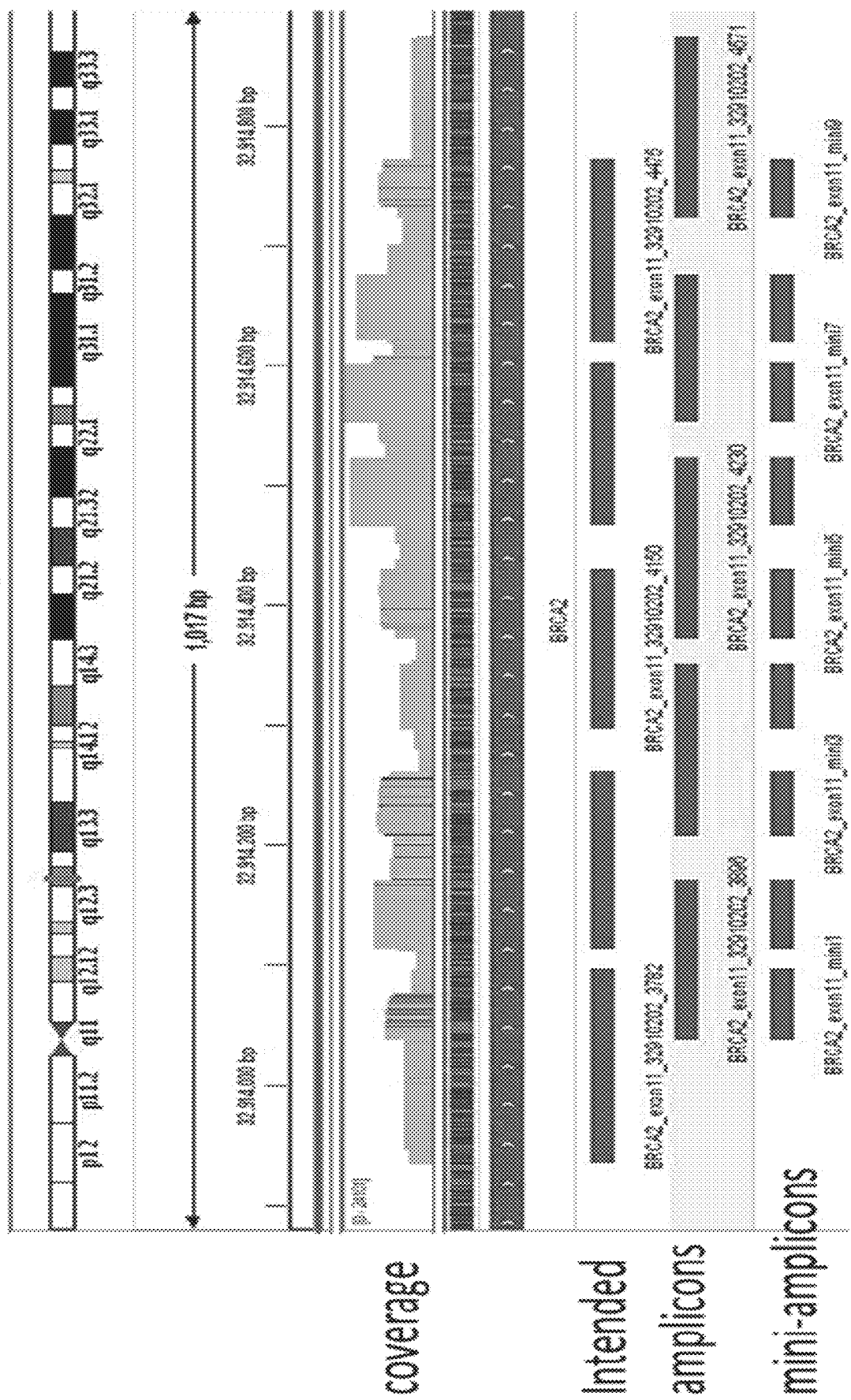
FIG. 12 depicts the coverage plot for the sequence data from Example 2. It is notable that coverage at the mini-amplicons is not significantly greater than the sum of the two overlapping intended amplicons.
Figure 13:
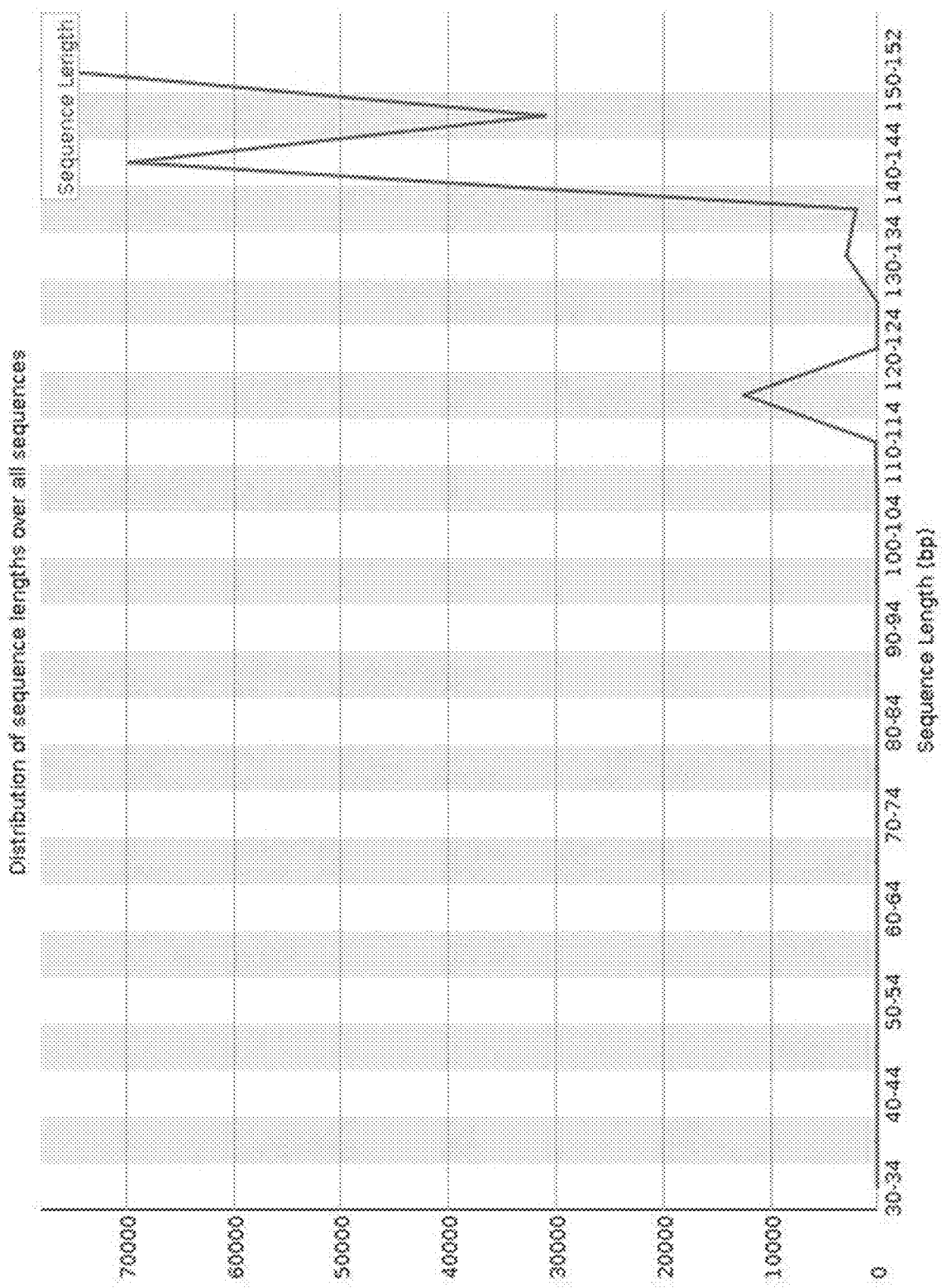
FIG. 13 depicts read lengths for the sequence data from Example 2. It is notable that there is not a significant number of short reads from primer dimers.

Results: The library quantification by Qubit was 49.9 nM. The GC-rich sequence was removed from the beginning of Read 2 for each read pair prior to aligning reads to the human genome and to the target region. The sequencing data was of high quality such that greater than 99% of reads aligned to the intended target regions. All 20 amplicons were represented in the final library and 95% of target bases were covered at greater than 20% of the mean coverage. FIG. 12 depicts the coverage of the BRCA2 region consisting of 10 overlapping amplicons. Mini-amplicons never show more coverage than the sum of the overlapping amplicons and therefore production of mini-amplicons are not a major contributor to coverage. This indicates that mini-amplicons do not dominate the library as they are suppressed by formation of a stable secondary structure. Primer dimers are also minimal in the final library such that short reads with an insert size of less than 35 bases represent less than 0.2% of the total reads (FIG. 13).

Conclusions: A targeted asymmetric amplicon library was successfully made using a synthetic GC-rich sequence introduced through one of the target specific primers as the first indexing primer sequence. The sequencing demonstrated that mini-amplicons produced from overlapping amplicon design and primer dimers did not contribute significantly to the final library.

TABLE 5

Oligonucleotides used in Example 2

| Sequence Name | SEQ ID NO | Sequence (5'-3') |
|---|---|---|
| 16-365 | 1 | TCAGACGTGTGCTCTTCCGAT*C*T |
| 17-754 | 46 | CAAGCAGAAGACGGCATACGAGATAATGAGCGGTGACTGGAGTTCAGACGTGTGCTCTTCCGATCTGCGCGCGG |
| 17-758 | 47 | AATGATACGGCGACCACCGAGATCTACACCCTATCCTACACTCTTTCCCTACACGACGCTCTTCCGATCT |

*Phosphorothioated DNA bases (IDT)

TABLE 6

Target-Specific Oligonucleotides used in Example 2

| SEQ ID NO | Sequence (5'-3') | Final concentration in PCR (nM) |
|---|---|---|
| 48 | CCCTACACGACGCTCTTCCGATCTGCGCGCGGTGATGGCAAATACACAGAGGAAG | 130 |
| 49 | CCCTACACGACGCTCTTCCGATCTCAGGATTCTTACAGAAAACAAGTGGT | 130 |

TABLE 6-continued

Target-Specific Oligonucleotides used in Example 2

| SEQ ID NO | Sequence (5'-3') | Final concentration in PCR (nM) |
|---|---|---|
| 50 | CCCTACACGACGCTCTTCCGATCTGCGCGCGGCAGAGTAACAGACTAGCTAGAGACAATG | 130 |
| 51 | CCCTACACGACGCTCTTCCGATCTAGCACTTACCTGTGACTCCATAG | 130 |
| 52 | CCCTACACGACGCTCTTCCGATCTGCGCGCGGGCCAGAACTACAATCTTTTGATGACA | 130 |
| 53 | CCCTACACGACGCTCTTCCGATCTATTGTGTGGAAGATCCAATCCAT | 130 |
| 54 | CCCTACACGACGCTCTTCCGATCTGCGCGCGGATTCACAGAGACTTGGCAGCC | 105 |
| 55 | CCCTACACGACGCTCTTCCGATCTGTCAAGCAGAGAATGGGTACTCAC | 105 |
| 56 | CCCTACACGACGCTCTTCCGATCTGCGCGCGGAGCTTGTGGAGCCTCTTACA | 130 |
| 57 | CCCTACACGACGCTCTTCCGATCTGGGACCTTACCTTATACACCGT | 130 |
| 58 | CCCTACACGACGCTCTTCCGATCTGCGCGCGGGATCCCAGAAGGTGAGAAAGTT | 105 |
| 59 | CCCTACACGACGCTCTTCCGATCTTGAGGTTCAGAGCCATGGA | 105 |
| 60 | CCCTACACGACGCTCTTCCGATCTGCGCGCGGCTCCAGGAAGCCTACGTGA | 105 |
| 61 | CCCTACACGACGCTCTTCCGATCTGGACATAGTCCAGGAGGCA | 105 |
| 62 | CCCTACACGACGCTCTTCCGATCTCACCGCAGCATGTCAAGATC | 255 |
| 63 | CCCTACACGACGCTCTTCCGATCTGCGCGCGGGACCTAAAGCCACCTCCTTAC | 255 |
| 64 | CCCTACACGACGCTCTTCCGATCTGCGCGCGGGGATCCAGACAACTGTTCAAACTG | 750 |
| 65 | CCCTACACGACGCTCTTCCGATCTGTTTTCCTTTACTTACTACACCTCA | 750 |
| 66 | CCCTACACGACGCTCTTCCGATCTGCGCGCGGGCATATTAAAACAAGATTTACCTCTATTG | 255 |
| 67 | CCCTACACGACGCTCTTCCGATCTATAAGGCCTGCTGAAAATGACTG | 255 |
| 68 | CCCTACACGACGCTCTTCCGATCTGCGCGCGGCTAGCTCTTCACCCTGCAAAAATA | 125 |
| 69 | CCCTACACGACGCTCTTCCGATCTGCGCGCGGAAAATCGTTTGTGTTTCACATGAAA | 125 |
| 70 | CCCTACACGACGCTCTTCCGATCTGCGCGCGGAGGAAAACAACGAGAATAAATCAAA | 125 |
| 71 | CCCTACACGACGCTCTTCCGATCTGCGCGCGGACTCTCTAGATAATGATGAATGTAGCA | 125 |
| 72 | CCCTACACGACGCTCTTCCGATCTGCGCGCGGTGTCTGGATTGGAGAAAGTTTCTAA | 125 |
| 73 | CCCTACACGACGCTCTTCCGATCTGCGCGCGGGTATAGGGAAGCTTCATAAGTCAGT | 125 |
| 74 | CCCTACACGACGCTCTTCCGATCTGCGCGCGGATTACAAACGCAAGACAAGTGTT | 125 |

TABLE 6-continued

Target-Specific Oligonucleotides used in Example 2

| SEQ ID NO | Sequence (5'-3') | Final concentration in PCR (nM) |
|---|---|---|
| 75 | CCCTACACGACGCTCTTCCGATCTGCGCGCGGATTCAGACCAGCTCACAAGAGAAG | 125 |
| 76 | CCCTACACGACGCTCTTCCGATCTGCGCGCGGAAGGCTTTTCATATAATGTGGTAAA | 125 |
| 77 | CCCTACACGACGCTCTTCCGATCTGCGCGCGGGAGTGTTAGAGGAATTTGATTTAA | 125 |
| 78 | CCCTACACGACGCTCTTCCGATCTCTGTCTGTAAATATGTCTTTCACT | 125 |
| 79 | CCCTACACGACGCTCTTCCGATCTAACAACCTGCCATAATTTTCGTTT | 125 |
| 80 | CCCTACACGACGCTCTTCCGATCTATGTCAGCAAAAACCTTATGTGAA | 125 |
| 81 | CCCTACACGACGCTCTTCCGATCTTTTCCAAACTAACATCACAAGGT | 125 |
| 82 | CCCTACACGACGCTCTTCCGATCTTGTGCTAAAAATCCCACAAGTATT | 125 |
| 83 | CCCTACACGACGCTCTTCCGATCTAAGACTTGCTTGGTACTATCTTCT | 125 |
| 84 | CCCTACACGACGCTCTTCCGATCTTTCTGGAGTACGTATAGCAGTATT | 125 |
| 85 | CCCTACACGACGCTCTTCCGATCTCTTGCTGTACTAAATCCAGAGAAA | 125 |
| 86 | CCCTACACGACGCTCTTCCGATCTTAGTGAAGACTATGCTCAGTTCTG | 250 |
| 87 | CCCTACACGACGCTCTTCCGATCTTTACTGCAGGTTTTTCCATTTCT | 250 |

Example 3

Rationale: A 50 amplicon hotspot panel was designed to cover common human single nucleotide polymorphisms (SNPs) where the forward target specific primer included a unique synthetic sequence different from the target sequence as the first indexing primer sequence for introduction of a barcoded Ion Torrent Adapter A sequence. The universal sequence was also a unique synthetic sequence different from both the target and Ion Torrent adapter sequences.

Materials:
Human genomic DNA (Coriell Institute, NA12878)
Q5® Hot Start High-Fidelity 2× Master Mix (NEB, cat #M0494)
100 target-specific primers (Table 8)
Universal primer 16-365 (Table 7)
Barcoded Adapter A primer 18-107 (Table 7)
Adapter P1 primer 18-111 (Table 7)
SPRIselect reagent (Beckman Coulter, B23318)
20% PEG-8000/2.5M NaCl solution
DNA Suspension Buffer, 10 mM Tris, 0.1 mM EDTA, pH 8.0 (Teknova, cat #T0227)
Qubit dsDNA HS Assay Kit (ThermoFisher Scientific, cat #Q32851)

Method: Human genomic DNA was diluted in DNA suspension buffer. A first reaction for target amplification and suppression PCR was performed in 30 µl. For each amplicon, both the forward and reverse target-specific primers contained the same universal primer sequence at the 5' end. The forward target-specific primers also contained a 17 bp insert between the universal primer sequence and the target specific portion of the primer as the first indexing primer sequence used for annealing of the barcoded Adapter A primer during indexing PCR. The reaction consisted of 1×Q5 Hot Start High-Fidelity Master Mix, a mix of 100 target-specific primers present at 4 nM each, 10 uM universal primer, and 10 ng genomic DNA. The following cycling program was run on this reaction mix: 30 seconds at 98° C. followed by 4 cycles of 10 seconds at 98° C., and 6 minutes at 66° C., then 18 cycles of 10 seconds at 98° C., 15 seconds at 60° C., and 1 minutes at 66° C., and completed with 1 minute at 65° C. A reaction clean-up was done with 36 µl of SPRIselect beads (1.2× ratio) and the beads were resuspended in 50 µl of a second reaction mix containing 1×Q5 Hot Start High-Fidelity Master Mix, 300 nM of the barcoded Adapter A primer containing the corresponding first indexing primer sequence at its 3' terminus, and 300 nM of the Adapter P1 primer containing the corresponding universal sequence at its 3' terminus. The following cycling program was run on this reaction mix: 45 seconds at 98° C. followed by 8 cycles of 10 seconds at 98° C., 15 seconds at 60° C., and 1 minute at 66° C. to add a sample barcode and NGS adapters to the amplicons. A reaction clean-up was performed with 26 μl of PEG-8000/2.5M NaCl solution (0.85× ratio) and the DNA was eluted in 20 μl DNA Suspension Buffer. Library was quantified using the Qubit dsDNA HS Assay Kit and sequenced with the Ion PGM™ System on a 318 Chip v2 (ThermoFisher Scientific).

Results: The library quantification by Qubit was 10.9 nM. Reads were aligned to the human genome and to the target region. The sequencing data was of high quality such that greater than 95% of reads aligned to the intended target regions and all 50 amplicons were represented in the final library. FIG. 14 depicts read length showing that the vast majority of reads are greater than 140 bases and indicting that short, primer dimer reads are not a major contributor to the final library.

Conclusions: A targeted asymmetric amplicon library was successfully made with Ion Torrent adapters through introduction of a synthetic sequence as the first indexing primer sequence on one of the target specific primers. The sequencing demonstrated that primer dimers did not contribute significantly to the final library.

It should be understood that the foregoing description provides embodiments of the present invention which can be varied and combined without departing from the spirit of this disclosure. To the extent that the different aspects disclosed can be combined, such combinations are disclosed herein.

TABLE 7

Oligonucleotides used in Example 3

| Sequence Name | SEQ ID NO | Sequence (5'-3') |
|---|---|---|
| 16-365 | 1 | TCAGACGTGTGCTCTTCCGAT*C*T |
| 18-107 | 88 | CCATCTCATCCCTGCGTGTCTCCGACTCAGCTAAGGTAACAGCAGGATCGGTATGGC |
| 18-111 | 89 | CCTCTCTATGGGCAGTCGGTGATTCAGACGTGTGCTCTTCCGATCT |

TABLE 8

Target-Specific Oligonucleotides used in Example 3

| SEQ ID NO | Sequence (5'-3') |
|---|---|
| 90 | TCAGACGTGTGCTCTTCCGATCTAGCAGGATCGGTATGGCAAGTATACCACTGACAGGGAAAC*A*A |
| 91 | TCAGACGTGTGCTCTTCCGATCTAACATTTTCCTGGATGTACTTGC*T*G |
| 92 | TCAGACGTGTGCTCTTCCGATCTAGCAGGATCGGTATGGCTGTGTTGTATTTCCAGCAGTTCA*A*A |
| 93 | TCAGACGTGTGCTCTTCCGATCTCTTCACAGCCTGCTATACCTACT*A*G |
| 94 | TCAGACGTGTGCTCTTCCGATCTAGCAGGATCGGTATGGCGAGGCTGATCATGAGGAATCTC*T*G |
| 95 | TCAGACGTGTGCTCTTCCGATCTTTCACCCAGTCTTCCATATCATT*C*T |
| 96 | TCAGACGTGTGCTCTTCCGATCTAGCAGGATCGGTATGGCGCACTTCTCCTACTTAGGTCACT*T*T |
| 97 | TCAGACGTGTGCTCTTCCGATCTGGGTTTTTACAATGAACAACACA*G*C |
| 98 | TCAGACGTGTGCTCTTCCGATCTAGCAGGATCGGTATGGCGACTGTTACTAGCGGGCTTTTCT*T*G |
| 99 | TCAGACGTGTGCTCTTCCGATCTCAAGCCAGCAACCACAGAA*A*C |
| 100 | TCAGACGTGTGCTCTTCCGATCTAGCAGGATCGGTATGGCGATGATGACATCCTGAGCCCA*A*G |
| 101 | TCAGACGTGTGCTCTTCCGATCTCAGATCTCTTCTCATAAGGGCAC*T*G |
| 102 | TCAGACGTGTGCTCTTCCGATCTAGCAGGATCGGTATGGCCACCCATCATCCCCACTC*A*C |
| 103 | TCAGACGTGTGCTCTTCCGATCTTCTGCTCCCTGGGATGAGA*A*G |
| 104 | TCAGACGTGTGCTCTTCCGATCTAGCAGGATCGGTATGGCTGTTGCTTGTCATTCTCCAGATC*T*A |
| 105 | TCAGACGTGTGCTCTTCCGATCTCAAAAGGAAATGGTGCCTTTTTC*A*G |
| 106 | TCAGACGTGTGCTCTTCCGATCTAGCAGGATCGGTATGGCTAGGGGCGTATCAAAACCAAGAA*T*A |
| 107 | TCAGACGTGTGCTCTTCCGATCTTGACTAGCTAGAGTATCAAAAGG*G*T |

TABLE 8-continued

Target-Specific Oligonucleotides used in Example 3

| SEQ ID NO | Sequence (5'-3') |
|---|---|
| 108 | TCAGACGTGTGCTCTTCCGATCTAGCAGGATCGGTATGGCAATCCCTCTCTACTTACCTGGTT*T*G |
| 109 | TCAGACGTGTGCTCTTCCGATCTTGTTTAGCAGGTTCAGGGTC*A*C |
| 110 | TCAGACGTGTGCTCTTCCGATCTAGCAGGATCGGTATGGCACCTTCTACTGTGTTCTTATAGG*C*A |
| 111 | TCAGACGTGTGCTCTTCCGATCTCAGTCAAGGATCTGTACTCTCCT*T*G |
| 112 | TCAGACGTGTGCTCTTCCGATCTAGCAGGATCGGTATGGCCCTCAACCAGAAAACATCAAGAT*T*T |
| 113 | TCAGACGTGTGCTCTTCCGATCTTGGCATTCTTTATCTTCACATCA*A*C |
| 114 | TCAGACGTGTGCTCTTCCGATCTAGCAGGATCGGTATGGCAAGCCACCACTGTGACC*A*C |
| 115 | TCAGACGTGTGCTCTTCCGATCTGACCTCCACCTCTAGGACC*T*G |
| 116 | TCAGACGTGTGCTCTTCCGATCTAGCAGGATCGGTATGGCAACAGAACGAAAAAGAAAGTGGC*T*C |
| 117 | TCAGACGTGTGCTCTTCCGATCTCTCAAACTGTGATAAGCTGCACT*T*G |
| 118 | TCAGACGTGTGCTCTTCCGATCTAGCAGGATCGGTATGGCTTCCCAAAGATGCAGAACTACAA*A*G |
| 119 | TCAGACGTGTGCTCTTCCGATCTGTGACTCAGACTTGTCCCA*G*G |
| 120 | TCAGACGTGTGCTCTTCCGATCTAGCAGGATCGGTATGGCAGACAGTAGTAATAACAGCAAGG*G*C |
| 121 | TCAGACGTGTGCTCTTCCGATCTCATTATGGGGATCTTCTTTGCCT*T*C |
| 122 | TCAGACGTGTGCTCTTCCGATCTAGCAGGATCGGTATGGCCCATAAGAAATGCCTGGGAAA*C*C |
| 123 | TCAGACGTGTGCTCTTCCGATCTGTAGAGAATGTGGCTTCATCC*T*C |
| 124 | TCAGACGTGTGCTCTTCCGATCTAGCAGGATCGGTATGGCGGGTACAAGTATGTGAAACAAAG*G*G |
| 125 | TCAGACGTGTGCTCTTCCGATCTCTCTGGACTTGTTGGAGAAGGCA*T*T |
| 126 | TCAGACGTGTGCTCTTCCGATCTAGCAGGATCGGTATGGCTGTTCTCTGGTAGTTCCTCTTC*A*G |
| 127 | TCAGACGTGTGCTCTTCCGATCTTTGTTTCTTAAAGGCTGCTCTTG*A*G |
| 128 | TCAGACGTGTGCTCTTCCGATCTAGCAGGATCGGTATGGCTCACACATAGCACACGTG*G*T |
| 129 | TCAGACGTGTGCTCTTCCGATCTATGCCGATGGGATTGACAT*G*G |
| 130 | TCAGACGTGTGCTCTTCCGATCTAGCAGGATCGGTATGGCTTTTGCATAACTTGGGGTGTAAG*A*G |
| 131 | TCAGACGTGTGCTCTTCCGATCTCTAGATCCCCAAACTTCTGCCT*T*C |
| 132 | TCAGACGTGTGCTCTTCCGATCTAGCAGGATCGGTATGGCGGGAGCATATTATGGCAGTG*G*A |
| 133 | TCAGACGTGTGCTCTTCCGATCTCACTGAGTTCTAAAATGCCAGAA*G*G |
| 134 | TCAGACGTGTGCTCTTCCGATCTAGCAGGATCGGTATGGCCTCAGGAGAAGAGACTCACAC*A*G |
| 135 | TCAGACGTGTGCTCTTCCGATCTTACCTAAGCACATTTAAAGGGGG*A*A |
| 136 | TCAGACGTGTGCTCTTCCGATCTAGCAGGATCGGTATGGCCTAAGATCAGCTCCCTTTGTCT*G*T |

TABLE 8-continued

Target-Specific Oligonucleotides used in Example 3

| SEQ ID NO | Sequence (5'-3') |
|---|---|
| 137 | TCAGACGTGTGCTCTTCCGATCTTTGGCAATGTAGACACTGGTC*A*G |
| 138 | TCAGACGTGTGCTCTTCCGATCTAGCAGGATCGGTATGGCGTACTCGTGTCTCACAGTGTG*T*C |
| 139 | TCAGACGTGTGCTCTTCCGATCTATTATTTCCCACCCTTCCCACTT*T*C |
| 140 | TCAGACGTGTGCTCTTCCGATCTAGCAGGATCGGTATGGCAGGGTTATAGGCACAAATTCTCC*T*T |
| 141 | TCAGACGTGTGCTCTTCCGATCTTGTCTTCGTTTTAATTGCCAAGC*A*G |
| 142 | TCAGACGTGTGCTCTTCCGATCTAGCAGGATCGGTATGGCCCAAACTGCATGACTCTCTTTGT*A*C |
| 143 | TCAGACGTGTGCTCTTCCGATCTGGCGGCAACAACAGATTGA*A*C |
| 144 | TCAGACGTGTGCTCTTCCGATCTAGCAGGATCGGTATGGCTAGGAAGAGTTAATCACGTGCTT*C*A |
| 145 | TCAGACGTGTGCTCTTCCGATCTATGAAGGCCTTATTTTCATCTGC*A*G |
| 146 | TCAGACGTGTGCTCTTCCGATCTAGCAGGATCGGTATGGCCACAGGACTATGACATCACCC*A*G |
| 147 | TCAGACGTGTGCTCTTCCGATCTCCTCACCTCAATTATAAAGTTGC*C*G |
| 148 | TCAGACGTGTGCTCTTCCGATCTAGCAGGATCGGTATGGCGGAGGAAAAGATACTCATCCCTT*C*T |
| 149 | TCAGACGTGTGCTCTTCCGATCTTTCTTGGCTATGGATGGAGTAA*G*C |
| 150 | TCAGACGTGTGCTCTTCCGATCTAGCAGGATCGGTATGGCTTTAGTTCTGTGCCTTCCCC*T*G |
| 151 | TCAGACGTGTGCTCTTCCGATCTGAGCAGGTAGAGCTGTGT*G*G |
| 152 | TCAGACGTGTGCTCTTCCGATCTAGCAGGATCGGTATGGCTGGATTCTTCTAGTTCCCGATAC*A*G |
| 153 | TCAGACGTGTGCTCTTCCGATCTCATAAACCCGTAATGTGAAGCC*T*G |
| 154 | TCAGACGTGTGCTCTTCCGATCTAGCAGGATCGGTATGGCACTTTCTTAATCCCTCCTCATGC*A*A |
| 155 | TCAGACGTGTGCTCTTCCGATCTCAACCTGAAATTGCTGCAGGA*A*G |
| 156 | TCAGACGTGTGCTCTTCCGATCTAGCAGGATCGGTATGGCGATGCTGGCAGGGGAGGCTGTAA*A*G |
| 157 | TCAGACGTGTGCTCTTCCGATCTCACAAGGACTGCAAGTTCCTGA*T*C |
| 158 | TCAGACGTGTGCTCTTCCGATCTAGCAGGATCGGTATGGCCTCCCCTTTTAG*T*A |
| 159 | TCAGACGTGTGCTCTTCCGATCTGTGGTTCCTTTTCAGGCACTATA*A*C |
| 160 | TCAGACGTGTGCTCTTCCGATCTAGCAGGATCGGTATGGCAGTCCTTGCCCTTCTTAATAAG*C*A |
| 161 | TCAGACGTGTGCTCTTCCGATCTCATAACAACTTCTTCAAGCTGCA*G*A |
| 162 | TCAGACGTGTGCTCTTCCGATCTAGCAGGATCGGTATGGCTGAGCGGAAATTAATCTTCAAGTT*T*T |
| 163 | TCAGACGTGTGCTCTTCCGATCTGTCATTCCAGATTTGTTGTGTGT*A*C |
| 164 | TCAGACGTGTGCTCTTCCGATCTAGCAGGATCGGTATGGCAGGAAAACAATTTAAGTAAGGAAACT*C*C |
| 165 | TCAGACGTGTGCTCTTCCGATCTTTTCCCATTACACTCCTTCAGAT*G*T |
| 166 | TCAGACGTGTGCTCTTCCGATCTAGCAGGATCGGTATGGCGAGAACTGAGCGAAGGGAAAA*G*A |

TABLE 8-continued

Target-Specific Oligonucleotides used in Example 3

| SEQ ID NO | Sequence (5'-3') |
|---|---|
| 167 | TCAGACGTGTGCTCTTCCGATCTCTGGTCCACAGTGTACCTAACT*T*C |
| 168 | TCAGACGTGTGCTCTTCCGATCTAGCAGGATCGGTATGGCTAAAGACATGAAGTACCCCATTG*C*T |
| 169 | TCAGACGTGTGCTCTTCCGATCTGATGTAGTAATGCATGCCATACA*G*C |
| 170 | TCAGACGTGTGCTCTTCCGATCTAGCAGGATCGGTATGGCCTTCATGTGTTAACCTGGGGATG*A*T |
| 171 | TCAGACGTGTGCTCTTCCGATCTTTAACAACTCTTGTCCAAAGAAG*G*C |
| 172 | TCAGACGTGTGCTCTTCCGATCTAGCAGGATCGGTATGGCATTTGGAACTGACTGTACTTTCT*G*C |
| 173 | TCAGACGTGTGCTCTTCCGATCTTACTCACCTCTGCCACTTGATC*T*T |
| 174 | TCAGACGTGTGCTCTTCCGATCTAGCAGGATCGGTATGGCCTCCCCCTCTTCATCATCTTCT*T*C |
| 175 | TCAGACGTGTGCTCTTCCGATCTTAGCTAGCATACTTCCTCACATG*T*G |
| 176 | TCAGACGTGTGCTCTTCCGATCTAGCAGGATCGGTATGGCTGTCTTTCCATGTGTCTTTATGC*T*G |
| 177 | TCAGACGTGTGCTCTTCCGATCTCATTCTCTCCAGTGGAAGAGAC*A*C |
| 178 | TCAGACGTGTGCTCTTCCGATCTAGCAGGATCGGTATGGCGAGGCCTCTGACTGTATCACTAT*T*T |
| 179 | TCAGACGTGTGCTCTTCCGATCTAAGCCAAGGGGTCTCTT*C*A |
| 180 | TCAGACGTGTGCTCTTCCGATCTAGCAGGATCGGTATGGCAGGTCAAATGGCAAAGGTAAAA*C*C |
| 181 | TCAGACGTGTGCTCTTCCGATCTCTGAGGATGGCAGCTGAGA*T*T |
| 182 | TCAGACGTGTGCTCTTCCGATCTAGCAGGATCGGTATGGCAAACATGATGGACAACAGAACTA*C*T |
| 183 | TCAGACGTGTGCTCTTCCGATCTCTGATTGGAGGGGCTGGTAA*A*G |
| 184 | TCAGACGTGTGCTCTTCCGATCTAGCAGGATCGGTATGGCGGAAGATTTAGAACAGCTGAAGC*A*G |
| 185 | TCAGACGTGTGCTCTTCCGATCTATCTTCCCTCGCCCCC*T*G |
| 186 | TCAGACGTGTGCTCTTCCGATCTAGCAGGATCGGTATGGCGGACTCATGTATGTCTACTGGAC*T*C |
| 187 | TCAGACGTGTGCTCTTCCGATCTCTTACCTCTTGACTGCCTGC*T*G |
| 188 | TCAGACGTGTGCTCTTCCGATCTAGCAGGATCGGTATGGCCAGTTCATTGAGTACTGTAAGCT*G*G |
| 189 | TCAGACGTGTGCTCTTCCGATCTGTGAAGGCAAAAAGGATGTCCA*A*G |

What is claimed is:

1. A next generation sequencing (NGS) kit comprising:
a first target-specific primer pair;
a second target-specific primer pair;
a universal primer comprising at least a portion of a universal sequence;
a first indexing primer comprising at least a portion of a first indexing primer sequence and a first adaptor sequence; and
a second indexing primer comprising at least a portion of the universal sequence and a second adaptor sequence, wherein the second indexing primer does not include the first indexing primer sequence, wherein the second adaptor sequence is different than the first adaptor sequence,
wherein the first target-specific primer pair comprises a first target-specific primer and a second target-specific primer,
wherein the first target-specific primer comprises, in a 3' to 5' orientation, a first target-specific sequence that is complementary to a first target sequence on a substrate nucleic acid molecule, the first indexing primer sequence and the universal sequence,
wherein the second target-specific primer comprises, in a 3' to 5' orientation, a second target-specific sequence that is complementary to a second target sequence on the substrate nucleic acid molecule and the universal sequence, wherein the second target-specific primer does not comprise the first indexing primer sequence,
wherein the second target-specific primer pair comprises a third target-specific primer and a fourth target-specific primer,
wherein the third target-specific primer comprises, in a 3' to 5' orientation, a third target-specific sequence that is complementary to a third target sequence on the substrate nucleic acid molecule, the first indexing primer sequence and the universal sequence,
wherein the fourth target-specific primer comprises, in a 3' to 5' orientation, a fourth target-specific sequence that is complementary to a fourth target sequence on the substrate nucleic acid molecule and the universal sequence, wherein the fourth target-specific primer does not comprise the first indexing primer sequence, and
wherein the first indexing primer sequence and the universal sequence are different from the first target-specific sequence, second target-specific sequence, third target-specific sequence and fourth target-specific sequence and from each other.

2. The NGS kit of claim 1, further comprising: deoxynucleoside triphosphates (dNTPs); and
a first DNA polymerase.

3. The NGS kit of claim 2, further comprising: a second DNA polymerase.

4. The NGS kit of claim 1, wherein the first indexing primer sequence consists of cytosine bases, guanine bases, or a combination thereof.

5. The NGS kit of claim 1, wherein the second target-specific primer comprises a first molecular identifier (MID) sequence.

6. The NGS kit of claim 5, wherein the fourth target-specific primer comprises a second molecule identifier (MID) sequence.

7. The NGS kit of claim 5, wherein the first MID sequence is positioned between the second target-specific sequence and the universal sequence.

8. The NGS kit of claim 6, wherein the first MID sequence is positioned between the second target-specific sequence and the universal sequence, wherein the second MID sequence is positioned between the fourth target-specific sequence and the universal sequence, or both.

9. The NGS kit of claim 1, wherein the first target-specific primer pair is sufficient to generate a first amplicon, wherein the second target-specific primer pair is sufficient to generate a second amplicon, and wherein a portion of the first amplicon overlaps with a portion of the second amplicon.

10. The NGS kit of claim 9, wherein the first amplicon overlaps with the second amplicon by no more than 100 nucleotides.

11. The NGS kit of claim 2, wherein the first DNA polymerase has 3' to 5' exonuclease activity and at least one of the first target-specific primer, the second target-specific primer, the third target-specific primer, the fourth target-specific primer, the first indexing primer, the second indexing primer and the universal primer comprises a 3' terminal nuclease-resistant modification.

12. The NGS kit of claim 11, wherein the 3' terminal nuclease-resistant modification is selected from the group consisting of a phosphorothioate linkage, a 2'0 methyl modification and a methylphosphonate modification.

13. The NGS kit of claim 3, wherein the second DNA polymerase has 3' to 5' exonuclease activity and at least one of the first indexing primer, the second indexing primer and the universal primer comprises a 3' terminal nuclease-resistant modification.

14. The NGS kit of claim 13, wherein the 3' terminal nuclease-resistant modification is selected from the group consisting of a phosphorothioate linkage, a 2'0 methyl modification and a methylphosphonate modification.

15. A method for next generation sequencing library preparation, comprising:
combining a first target-specific primer pair, a second target-specific primer pair, a substrate nucleic acid molecule, deoxynucleoside triphosphates (dNTPs), a first DNA polymerase, and a universal primer in a single reaction vessel to yield a first polymerase chain reaction (PCR) mixture;
subjecting the first PCR mixture to a series of PCR cycles under conditions sufficient to:
(a) generate target-specific amplicons from the first target-specific primer pair and the second-target specific primer pair, and
(b) amplify the target-specific amplicons from the universal primer,
wherein the first target-specific primer pair comprises a first target-specific primer and a second target-specific primer,
wherein the first target-specific primer comprises, in a 3' to 5' orientation, a first target-specific sequence that is complementary to a first target sequence on the substrate nucleic acid molecule, a first indexing primer sequence and a universal sequence,
wherein the second target-specific primer comprises, in a 3' to 5' orientation, a second target-specific sequence that is complementary to a second target sequence on the substrate nucleic acid molecule and the universal sequence, wherein the second target-specific primer does not comprise the first indexing primer sequence,
wherein the second target-specific primer pair comprises a third target-specific primer and a fourth target-specific primer,
wherein the third target-specific primer comprises, in a 3' to 5' orientation, a third target-specific sequence that is complementary to a third target sequence on the substrate nucleic acid molecule, the first indexing primer sequence and the universal sequence,
wherein the fourth target-specific primer comprises, in a 3' to 5' orientation, a fourth target-specific sequence that is complementary to a fourth target sequence on the substrate nucleic acid molecule and the universal sequence, wherein the fourth target-specific primer does not comprise the first indexing primer sequence,
wherein the universal primer comprises at least a portion of the universal sequence, and
wherein the first indexing primer sequence and the universal sequence are different from the first target-specific sequence, second target-specific sequence, third target-specific sequence and fourth target-specific sequence and from each other.

16. The method of claim 15, further comprising after the series of PCR cycles:
purifying the target-specific amplicons from the first PCR mixture to yield a pre-indexing sample.

17. The method of claim 16, further comprising:
combining the pre-indexing sample, a first indexing primer, a second indexing primer and, optionally, deoxynucleoside triphosphates (dNTPs) and a second DNA polymerase to yield a second PCR mixture; and
subjecting the second PCR mixture to an additional series of PCR cycles under conditions sufficient to generate asymmetrical amplicons from the first indexing primer and the second indexing primer,
wherein the first indexing primer comprises, in a 3' to 5' orientation, at least a portion of the first indexing primer sequence and a first adaptor sequence,
wherein the second indexing primer comprises, in a 3' to 5' orientation, at least a portion of the universal sequence and a second adaptor sequence, wherein the second indexing primer does not include the first indexing primer sequence, and wherein the second adaptor sequence is different than the first adaptor sequence.

18. The method of claim 17, further comprising:
purifying the asymmetrical amplicons from the second PCR mixture; and
sequencing the asymmetrical amplicons.

19. The method of claim 15, wherein the first DNA polymerase has 3' to 5' exonuclease activity, and wherein at least one of the first target-specific primer, the second target-specific primer, the third target-specific primer, the fourth target-specific primer and the universal primer comprises a 3' terminal nuclease-resistant modification.

20. The method of claim 19, wherein the 3' terminal nuclease-resistant modification is selected from the group consisting of a phosphorothioate linkage, a 2'0 methyl modification and a methylphosphonate modification.

* * * * *